US009552718B2

(12) United States Patent
Fadell et al.

(10) Patent No.: US 9,552,718 B2
(45) Date of Patent: *Jan. 24, 2017

(54) SMART-HOME HAZARD DETECTOR PROVIDING NON-ALARM STATUS SIGNALS AT OPPORTUNE MOMENTS

(71) Applicant: Google Inc., Mountain View, CA (US)

(72) Inventors: Anthony M. Fadell, Portola Valley, CA (US); Matthew L. Rogers, Los Gatos, CA (US); David Sloo, Menlo Park, CA (US); Maxime Veron, San Jose, CA (US); Sophie Le Guen, Burlingame, CA (US); Yoky Matsuoka, Palo Alto, CA (US); Jeffrey A. Boyd, Novato, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,912

(22) Filed: Mar. 10, 2015

(65) Prior Publication Data

US 2015/0187200 A1  Jul. 2, 2015

Related U.S. Application Data

(63) Continuation of application No. 14/508,047, filed on Oct. 7, 2014, now Pat. No. 9,007,224.
(Continued)

(51) Int. Cl.
*G08B 17/10* (2006.01)
*G08B 25/00* (2006.01)
(Continued)

(52) U.S. Cl.
CPC ......... *G08B 25/008* (2013.01); *F24F 11/0009* (2013.01); *G01N 27/02* (2013.01);
(Continued)

(58) Field of Classification Search
CPC ......... G08B 17/00; G08B 17/06; G08B 17/10; G08B 17/103; G08B 17/107; G08B 17/117; G08B 21/14; G08B 21/182; G08B 29/02; G08B 29/04; F24F 11/0009; G01N 33/0063
(Continued)

(56) References Cited

U.S. PATENT DOCUMENTS 5,309,145 A * 5/1994 Branch ................ G08B 19/005
340/540
6,876,305 B2  4/2005 Kadwell et al.
(Continued)

OTHER PUBLICATIONS

International Search Report & Written Opinion mailed Oct. 7, 2014, for International Patent Application No. PCT/US2014/059460, 11 pages.
(Continued)

*Primary Examiner* — Hung T Nguyen
(74) *Attorney, Agent, or Firm* — Kilpatrick Townsend & Stockton LLP

(57) ABSTRACT

A hazard detector may include a light sensor that senses a brightness level in an ambient environment. The hazard detector can have a processing system that receives an indication of the brightness level in the ambient environment from the light sensor. The processing system may then determine whether illumination in the ambient environment has been dimmed. Responsive to the dimming, the processing system may access information representative of a status of one or more components of the hazard detector. An illumination state may then be selected from a plurality of illumination states based on the accessed information representative of the status of the one or more components of the hazard detector. A light may then be illuminated based on the selected illumination state.

20 Claims, 22 Drawing Sheets

Related U.S. Application Data

(60) Provisional application No. 61/887,969, filed on Oct. 7, 2013, provisional application No. 61/887,963, filed on Oct. 7, 2013.

(51) Int. Cl.

| | |
|---|---|
| G08B 21/18 | (2006.01) |
| G01N 27/02 | (2006.01) |
| G01N 27/12 | (2006.01) |
| G01N 33/00 | (2006.01) |
| G08B 17/117 | (2006.01) |
| G08B 29/18 | (2006.01) |
| G08B 5/36 | (2006.01) |
| G08B 3/10 | (2006.01) |
| G08B 21/14 | (2006.01) |
| H04L 12/28 | (2006.01) |
| G08B 5/22 | (2006.01) |
| G08B 21/12 | (2006.01) |
| F24F 11/00 | (2006.01) |
| G08B 25/01 | (2006.01) |
| G08B 29/02 | (2006.01) |
| G08B 29/04 | (2006.01) |
| G08B 29/26 | (2006.01) |
| G08B 25/08 | (2006.01) |

(52) U.S. Cl.
CPC ......... *G01N 27/121* (2013.01); *G01N 33/004* (2013.01); *G01N 33/0031* (2013.01); *G08B 3/10* (2013.01); *G08B 5/22* (2013.01); *G08B 5/36* (2013.01); *G08B 17/10* (2013.01); *G08B 17/117* (2013.01); *G08B 21/12* (2013.01); *G08B 21/14* (2013.01); *G08B 21/18* (2013.01); *G08B 21/182* (2013.01); *G08B 25/002* (2013.01); *G08B 25/012* (2013.01); *G08B 29/02* (2013.01); *G08B 29/04* (2013.01); *G08B 29/185* (2013.01); *G08B 29/26* (2013.01); *H04L 12/2803* (2013.01); *H04L 12/2818* (2013.01); *G08B 25/08* (2013.01)

(58) Field of Classification Search
USPC ............ 340/506, 539.1, 540, 541, 577, 584, 588, 340/628, 630, 632
See application file for complete search history.

(56) References Cited

U.S. PATENT DOCUMENTS

| | | | |
|---|---|---|---|
| 6,912,429 B1* | 6/2005 | Bilger | G08B 25/008 236/49.3 |
| 7,378,976 B1 | 5/2008 | Paterno | |
| 7,649,472 B1 | 1/2010 | Paterno | |
| 8,172,154 B1 | 5/2012 | Figley | |
| 9,007,224 B1 | 4/2015 | Fadell et al. | |
| 2003/0038726 A1 | 2/2003 | Yoshida et al. | |
| 2004/0140892 A1 | 7/2004 | Hanood | |
| 2007/0285262 A1 | 12/2007 | Lax | |
| 2010/0052574 A1 | 3/2010 | Blakeley et al. | |
| 2011/0010041 A1 | 1/2011 | Wagner et al. | |
| 2012/0050051 A1 | 3/2012 | Clossen-von Lanken Schulz | |
| 2012/0126975 A1 | 5/2012 | Gonzales | |
| 2013/0169430 A1 | 7/2013 | Shook | |
| 2014/0085093 A1 | 3/2014 | Mittleman | |
| 2014/0375206 A1* | 12/2014 | Holland | H02J 9/061 315/86 |
| 2015/0077737 A1 | 3/2015 | Belinsky | |
| 2015/0097680 A1 | 4/2015 | Fadell et al. | |

OTHER PUBLICATIONS

Non-Final Office Action Mailed on Jun. 13, 2016, for U.S. Appl. No. 14/508,067, 31 pages.

Notice of Publication of Application dated Apr. 9, 2015, for U.S. Appl. No. 14/508,067.

* cited by examiner

| Speed | Meaning |
|---|---|
| SLOW | Low urgency |
| FAST | Increased urgency |
| ALARM | Maximum urgency |

1220

| Animation | Meaning |
|---|---|
| ○ | "Here's my status" |
| ↻ | "I need your attention" |
| ⊘ | "Ok" |
| ❂ | "Hi" |

1210

| Color | Meaning |
|---|---|
| (vertical lines) | Hello / confirmation / message |
| (crosshatch) | Everything's "Ok" |
| (diagonal lines) | Something may be wrong |
| (horizontal lines) | Something is definitely wrong |
| (dotted) | Let me help you |

1200

| Color | ◯ Pulse | ⟲ Rotate | 〜 Wave | ❀ Shimmer | ◉ On/Off |
|---|---|---|---|---|---|
| ▥ 1301 | Alarm or test | | | | |
| ▦ 1302 | Heads Up | Battery Low<br>Battery Critical | | | |
| ▨ 1303 | Lights out (no problems) | Connected to client<br>Test completed (all OK)<br>Post-alarm (All Right) | | | |
| ▤ 1304 | Choose Language<br>Button Pressed<br>Doorbell<br>Lights out (problems exist) | Ready for connections<br>Countdown to test<br>Reset<br>Shutdown begin<br>Shutdown countdown | Problem Description | Starting up | |
| ▦ 1305 | | | | | Night Light |

SMART-HOME HAZARD DETECTOR PROVIDING NON-ALARM STATUS SIGNALS AT OPPORTUNE MOMENTS

CROSS REFERENCES

This application is a continuation of U.S. application Ser. No. 14/508,047, filed Oct. 7, 2014, now U.S. Pat. No. 9,007,224, entitled "Smart-Home Hazard Detector Providing Non-Alarm Status Signals At Opportune Moments," which claims priority to U.S. Provisional Application No. 61/887,969, filed Oct. 7, 2013 entitled "User-Friendly Detection Unit," and claims priority to U.S. Provisional Application No. 61/887,963, filed Oct. 7, 2013 which are each hereby incorporated by reference for all purposes.

BACKGROUND

Hazard detection devices, such as smoke alarms and carbon monoxide alarms, help alert home or building occupants to the presence of danger but typically leave much to be desired in the realm of usability. For example, in many conventional hazard detection devices, when an installed battery's charge is low, the hazard detection device will periodically emit a chirp or other sound to alert nearby persons to the low battery charge condition. Frequently, this sound will initiate being produced by the hazard detection device during the night, waking nearby persons from sleep and potentially sending them on a hunt through their dwelling for the offending hazard detection device. Further, in order to test the functionality of a conventional hazard detection device, it is typically required to press a button located on the hazard detection device. Such an arrangement may be inefficient, such as if the hazard detection device is located in an inconvenient place.

FIELD

This patent specification relates to systems, devices, methods, and related computer program products for smart buildings including the smart home. More particularly, this patent specification relates to detection units, such as hazard detection units (e.g., smoke detectors. carbon monoxide sensors, etc.) or other monitoring devices, that are useful in smart building and smart home environments.

SUMMARY

Various systems, devices, apparatuses, methods, computer readable mediums are presented that allow for the presentation of statuses of a hazard detector. Such a status may be presented in the form of an illuminated light using one or more colors and animations. Such a status may be presented when the brightness level in an environment drops below a threshold level.

In some embodiments a hazard detector is presented that include at least one hazard detection sensor that detects a presence of at least one type of hazard. The hazard detector may include a light sensor that senses a brightness level in an ambient environment of the hazard detector. The hazard detector may include a light. The hazard detector may include a processing system provided in operative communication with the at least one hazard detection sensor, the light sensor, and the light. The processing system may be configured to receive an indication of the brightness level in the ambient environment of the hazard detector from the light sensor. The processing system may be configured to determine the brightness level in the ambient environment of the hazard detector has reached a threshold value. The processing system may be configured to perform a status check of one or more components of the hazard detector. The processing system may be configured to select an illumination state from a plurality of illumination states based on the status check wherein each illumination state of the plurality of illumination states is assigned to a status associated with the hazard detector. The processing system may be configured to cause the light to illuminate using the selected illumination state of the plurality of illumination states in response to the determining the brightness level in the ambient environment of the hazard detector has reached the threshold value.

Embodiments of such a hazard detector may include one or more of the following features: The at least one hazard detection sensor may include a smoke detection sensor and a carbon monoxide detection sensor. The processing system being configured to perform the status check of the one or more components of the hazard detector may include the processing system being configured to determine that a battery charge of a battery of the hazard detector is below a threshold charge level, wherein the illumination state is indicative of a low battery condition. Each illumination state of the plurality of illumination states may include at least a color and an animation pattern. The processing system may be configured to gradually increase a brightness level of the light for at least 0.5 seconds; maintain the brightness level of the light for at least 0.5 seconds; and gradually decrease the brightness level of the light for at least 0.5 seconds. The hazard detector may include wireless transceiver configured to communicate with a wireless network, wherein the processing system is further configured to transmit a request to a remote server system accessible via the wireless transceiver and the Internet. The processing system may be configured to receive a notification from the remote server system via the wireless transceiver, wherein the illumination state is selected by the processing system based on the status check of the one or more components of the hazard detector and the notification from the remote server system received via the wireless transceiver. The hazard detector may include a plurality of light emitting diodes (LEDs) that output light from the hazard detector in a circular pattern. The hazard detector may include a button configured to be actuated by a user to initiate a function of the hazard detector, wherein the plurality of LEDs are arranged to output light from the hazard detector in the circular pattern encircling the button. The processing system may be configured to determine whether at least a threshold time period has elapsed since previously causing the light to illuminate in response to determining the lighting condition is indicative of the brightness level in the ambient environment of the hazard detector reaching the threshold value. The processing system may be configured to cause the light to illuminate based on the illumination state and further based on at least the threshold time period having been determined to have elapsed. The hazard detector may include a motion detection sensor that senses motion in the ambient environment of the hazard detector, wherein the processing system is further configured to cause the light to illuminate based on the motion detector indicating motion is present in the ambient environment of the hazard detector and the lighting condition indicative of the brightness level in the ambient environment of the hazard detector reaching the threshold value. The processing system may be configured to cause the light to illuminate based on the motion detector indicating motion is present in the ambient environment of the hazard detector, the lighting condition indicative of the brightness level in the ambient environment of the hazard detector reaching the threshold value, and a user-defined setting stored by the processing system indicative of the hazard detector being not inside a bedroom.

In some embodiments, a hazard detector apparatus is presented. The apparatus may include means for measuring a brightness level in the ambient environment of the hazard detector. The apparatus may include means for determining the brightness level in the ambient environment of the hazard detector has reached a stored threshold value. The apparatus may include means for performing a status check of one or more components of the hazard detector. The apparatus may include means for selecting an illumination state from a plurality of illumination states based on the status check wherein each illumination state of the plurality of illumination states is assigned to a status associated with the hazard detector. The apparatus may include means for illuminating using the selected illumination state of the plurality of illumination states in response to determining the brightness level in the ambient environment of the hazard detector has reached the threshold value.

Further the apparatus may include means for wirelessly communicating with a wireless network, to transmit a request to a remote server system accessible via the wireless network and the Internet. The apparatus may include means for receiving, via the wireless network, a notification from the remote server system. The illumination state is selected may be based on the status check and the notification from the remote server system received via the wireless network.

BRIEF DESCRIPTION OF THE DRAWINGS

A further understanding of the nature and advantages of various embodiments may be realized by reference to the following figures. In the appended figures, similar components or features may have the same reference label.

FIG. 12 illustrates embodiments of definitions for visual effects that may be used by a hazard detector.

FIG. 13 illustrates various combinations of visual effects and color that may be used by a hazard detector.

DETAILED DESCRIPTION

Figure 1:
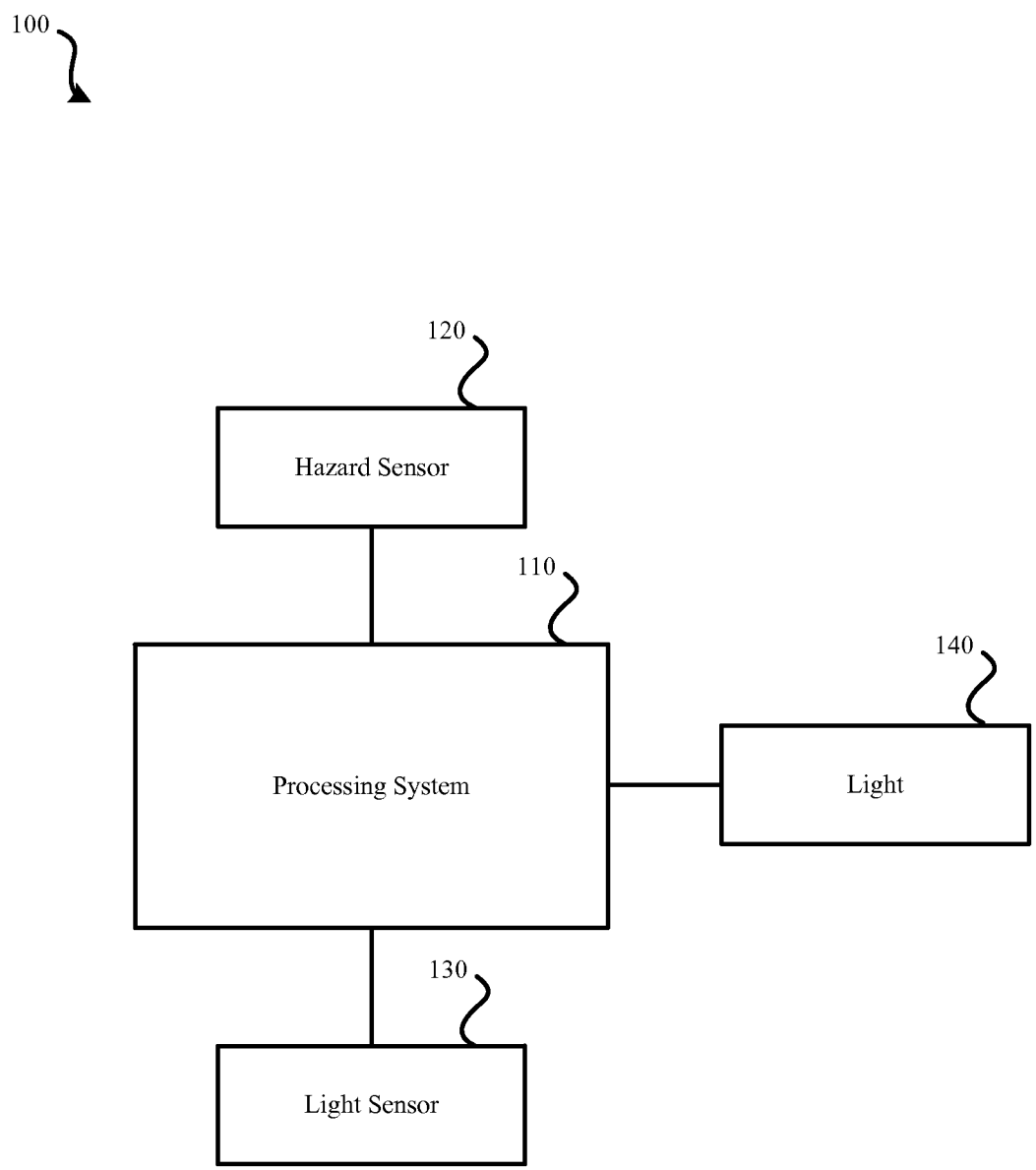
FIG. 1 illustrates a block diagram of an embodiment of a hazard detector.

Hazard detectors may include smoke detectors, carbon monoxide detectors, and/or other forms of detectors that can detect the presence of a hazard. For instance, a hazard detector may be a combined smoke and carbon monoxide detector configured to be installed on a wall or ceiling in a room, such as a room of a home (e.g., bedroom, office, kitchen, hallway, etc.) or other type of structure. It may be beneficial for such a hazard detector to provide a user with information regarding the functioning of the hazard detector. For the purposes of this document, a user refers to a person who is in the vicinity of the hazard detector and/or is interacting with the hazard detector. The hazard detector may provide a user with status information, such as the result of a battery test that determines if the battery has sufficient charge, has a low charge, or needs to be replaced immediately. In a conventional hazard detector, whenever a low battery condition is detected, the hazard detector may commence emitting a periodic noise, such as a loud chirp, to alert nearby users to the low battery condition. In contrast to such a conventional arrangement, information regarding a status of the hazard detector may be presented by embodiments of a hazard detector detailed herein in response to environmental conditions.

Such environmental conditions may be indicative of a user leaving a room, potentially for the last time on a given day (or going to bed). The hazard detector may monitor the lighting conditions of its ambient environment and determine when the amount of ambient light has dropped below a threshold level. Such a drop in ambient light may be indicative of a user shutting one or more lights off in the vicinity of the hazard detector. Further, the ambient light dropping below the threshold level may be indicative of evening and a dearth of natural light being present in the ambient environment of the hazard detector. In response to the hazard detector detecting that the amount of light present in its vicinity has dropped below the threshold level, either performance of a status check may be triggered or presentation of the results of a status check may be triggered to be presented. The status check may check various conditions of the hazard detector, such as the battery charge level, connectivity to a remote server, whether any messages are pending for a user of the hazard detector (e.g., at the remote server), whether the smoke sensor and/or carbon monoxide sensor is functioning properly, whether the effective life of the hazard detector has expired, whether a full test of the hazard detector should be performed, whether wired power is being received by the hazard detector, whether connectivity to a wireless network is present, and/or other conditions of the hazard detector.

Regardless of whether the status check is performed prior to or in response to the ambient light of the hazard detector dropping to the threshold value, the drop in ambient lighting may trigger the hazard detector to visually present a result of the status check. Color, animation patterns, and/or a speed of presentation may be used to convey information to a user. For instance, green light may be presented to the user for a brief time following the lighting condition reaching the threshold brightness level. Such green light may be indicative of the status check identifying no issues that need action from a user. If yellow light is displayed instead, this may be indicative of the status check determining one or more issues, such as a low battery condition, require action from the user. Yellow light may be indicative of actions that are not needed immediately. Red light may be indicative of the status check determining one or more issues need to be dealt with by the user immediately, such as a missing battery or a damaged sensor. The use of light to provide the status may be especially useful to avoid being overly intrusive to users in the vicinity of the hazard detector. For instance, the status check of the hazard detector could be ignored by an uninterested user simply by not looking at the hazard detector. Thus, for some embodiments, it has been found particularly advantageous to provide an optical signal, such as the light signal described above, while particularly avoiding the provision of an accompanying alerting sound signal, for non-alarm status notifications. While sound signals are certainly a necessary part of alarm-level conditions in which a hazardous condition is actually detected, it has been found to be more advantageous not to use sound signals, and to use more subtle signals such as light-only signals, for certain circumstances of lesser importance. In some scenarios this can have very advantageous consequences in comparison to alternative scenarios. For example, it can be the case that a hazard detector emitting the dreaded low-battery 'chirp' might simply be removed from the wall by an irritated, sleepy user and set on the floor or table with the battery compartment hastily opened and the battery removed. This is a clearly disadvantageous situation since there is then no hazard detection at all for that location until such time as the user, perhaps the following day (hopefully), reinstalls a fresh battery and places the unit back in its proper location. In contrast, by using a mildly alerting optical signal (such as a yellow light) while withholding the irritating chirp for situations in which the battery is starting to get low, the user will know that something needs attention when they see that yellow color, but the situation of disablement by an irritated, sleepy user can be avoided so that there is proper hazard detection taking place at all times. As another advantage, the provision of a brief, silent green light (or other silent but visually reassuring signal) can provide a pleasing sense of reassurance for the user, without being irritated or interfering. For example, for the situation of a mother who has just put her young child to bed and is turning out the lights for the night, the brief, silent, pleasant green glow can provide a satisfying sense of well-being and reassurance. Notably, at the same, there is a constructive recurring pattern of cognition being built up, whether it be in the conscious mind or the subconscious mind, in that there will be an expectation that the green glow will occur when the light is turned out, such that if the green glow is replaced by a yellow glow, it will be all the more noticeable. It is to be appreciated that the features and advantages of the preferred embodiments are best applied in the context of a battery that is starting to get low, but that is not too low. In accordance with governmental safety standards, it is preferable to continue to provide the unpleasant chirping sound when the battery gets too low. However, when implemented according to one or more of the preferred embodiments described herein, it is substantially less probable that the hazard detector will ever get to the "too low" condition, as there will have likely been several opportunities for the user to have already changed the battery upon seeing and responding to the silent yellow-light alerts that will have occurred over several days or weeks.

Once a status has been presented, the light on the hazard detector may shut off or may fade to off. Once the status has been presented, the hazard detector may be configured to not present the status again until at least a predefined period of time has elapsed (e.g., 1 hour, 4 hours, 20 hours, 1 day, etc.). In some embodiments, the hazard detector may be configured to provide ambient lighting if motion is detected in the vicinity of the hazard detector, the ambient lighting is below the threshold, and the hazard detector is configured to provide such light (e.g., the hazard detector has received input indicating it is not present in a bedroom). The same light which output the status may be used to provide ambient lighting, possibility using a different color, such as white light.

If a user views the status presented by the hazard detector and is satisfied with the status or is otherwise uninterested, the user may perform no other action, may simply leave the room, may go to bed, or otherwise may continue about his or her day. However, in some situations, the user may desire more information about the status. For instance, if the hazard detector presents a yellow status, the user may desire to learn one or more details about the status. For a predetermined period of time after the status has been presented, the hazard detector may activate a motion detector that can determine if the user has performed any gestures in the vicinity of the hazard detector. For instance, if the hazard detector is attached to the ceiling, below the hazard detector or otherwise nearby, the user may wave one time or multiple times to trigger the hazard detector to provide detail about the previously-displayed status. If the gesture is detected, rather than outputting a visual indicator, the hazard detector may output an auditory message. For instance, the auditory message may be a spoken message that indicates further detail about the status of the hazard detector. As an example, the hazard detector may state "The battery is low. Please replace the battery at your earliest convenience." The ability to use a gesture to trigger the detail about the status to be spoken to the user may be useful especially if the hazard detector is out of reach, such as mounted to a ceiling.

FIG. 1 illustrates a block diagram of an embodiment of a hazard detector 100. Hazard detector 100 may include: processing system 110, hazard sensor 120, light sensor 130, and light 140. It should be understood that this block diagram is a simplification of hazard detector 100; other components may be present. For instance, hazard detector 100 requires some form of power source. As another example, hazard detector 100 likely includes some form of sound creator configured to make a loud noise when the presence of the hazard is detected by hazard sensor 120.

Hazard sensor 120 may be configured to detect a particular type of hazard in the vicinity of hazard detector 100. For instance, hazard sensor 120 may be configured to detect the presence of smoke or the presence of carbon monoxide in the vicinity of hazard detector 100. While hazard detector 100 is illustrated as having a single hazard sensor 120, it should be understood that multiple hazard sensors may be present. For instance, hazard detector 100 may include both a smoke sensor and a carbon monoxide sensor. In some embodiments, multiple forms of smoke sensors may be present. For instance, an ionization-based smoke sensor may be present and also a photoelectric smoke sensor may be present. Each of such types of smoke sensor may be preferable for detecting various forms of fires (e.g., fast-flaming fires, slow smoldering fires). It should be understood that other forms of hazard sensors may be possible to use as hazard sensor 120; for example, hazard sensor 120 may be configured to detect the presence of ammonium, volatile organic compounds, humidity, temperature, or any other environmental condition which may pose a threat to users or equipment in the vicinity. Whether one or more hazard sensors are present, data may be transferred to processing system 110. For example, if hazard sensor 120 detects the presence of smoke, data indicating the presence of smoke may be transferred to processing system 110 by hazard sensor 120. Hazard sensor 120 may also be able to provide processing system 110 with additional information, such as data indicating whether hazard sensor 120 is functioning properly. In some embodiments, it may be possible for processing system 110 to transmit a signal to hazard sensor 120 that causes hazard sensor 120 to perform a self-test.

Light sensor 130 may be configured to detect a brightness level of light in the ambient environment of hazard detector 100. Light sensor 130 may provide data to processing system 110 that indicates a brightness of the ambient environment of hazard detector 100. In some embodiments, rather than providing a brightness level to processing system 110, light sensor 130 may indicate to processing system 110 when a threshold brightness level has been reached by the brightness of the ambient environment of hazard detector 100. In some embodiments, the threshold brightness value may be monitored for when the brightness drops below the threshold brightness value to trigger the status check of hazard detector 100.

Light 140 may include one or more lighting elements, such as light emitting diodes (LEDs), that are configured to output multiple colors of light. Further, light 140 may be configured to output various patterns of light. For example, light 140 may be configured to output green, yellow, red, blue, and white light. Further, light 140 may be configured to flash, produce a circulation effect (as will be further described in this document, also referred to as a halo-sweep effect), and/or fade on and off.

Processing system 110 may be in communication with hazard sensor 120, light sensor 130, and the light 140. Processing system 110 may include one or more processors configured to receive data from hazard sensor 120 and light sensor 130, and configured to control illumination of light 140. Processing system 110 may receive data from light sensor 130. Processing system 110 may be configured to use the data received from light sensor 130 to determine when the brightness in the ambient environment of hazard detector 100 has dropped below a threshold brightness level. Therefore, processing system 110 may store the threshold brightness level used for the comparison with brightness information received in the data from light sensor 130. Processing system 110 may also be configured to monitor when the last time a status check was performed and/or when was the last time the brightness level in the ambient environment of hazard detector 100 dropped below the threshold brightness level. In some embodiments, processing system 110 periodically performs a status check of one or more components of hazard detector 100 (and, possibly, checks an account of the user of hazard detector 100 stored by a remote server). In some embodiments, rather than periodically performing the status check, processing system 110 may perform the status check in response to the ambient brightness detected by light sensor 130 dropping below the threshold brightness level.

Processing system 110 may be configured to check the status of hazard sensor 120. For instance, processing system 110 may be configured to query hazard sensor 120 to determine if hazard sensor 120 is functioning properly. In some embodiments, processing system 110 is configured to determine if hazard sensor 120 has expired (for example, smoke detectors may be considered only functional for a predetermined amount of time, such as seven years).

Processing system 110 may be configured to check the status of one or more components of hazard detector 100 in addition to or alternatively to hazard sensor 120. For instance, processing system 110 may be configured to check a battery level of an onboard battery of hazard detector 100. In response to the status check performed by processing system 110, processing system 110 may be configured to determine a light color animation pattern, and/or speed that corresponds to the determined status. Processing system 110 may cause light 140 to illuminate according to the determined light color, pattern, and/or speed. Light 140 may be lit according to the light color, pattern, and/or speed for a predetermined amount of time, such as two or three seconds in order to convey the result of the status check to a user in the vicinity of hazard detector 100. In some embodiments, the status is presented as part of a one second fade in, one second at full brightness, and one second fade out animation of the light. Such a quick presentation may help preserve battery life.

Figure 2:
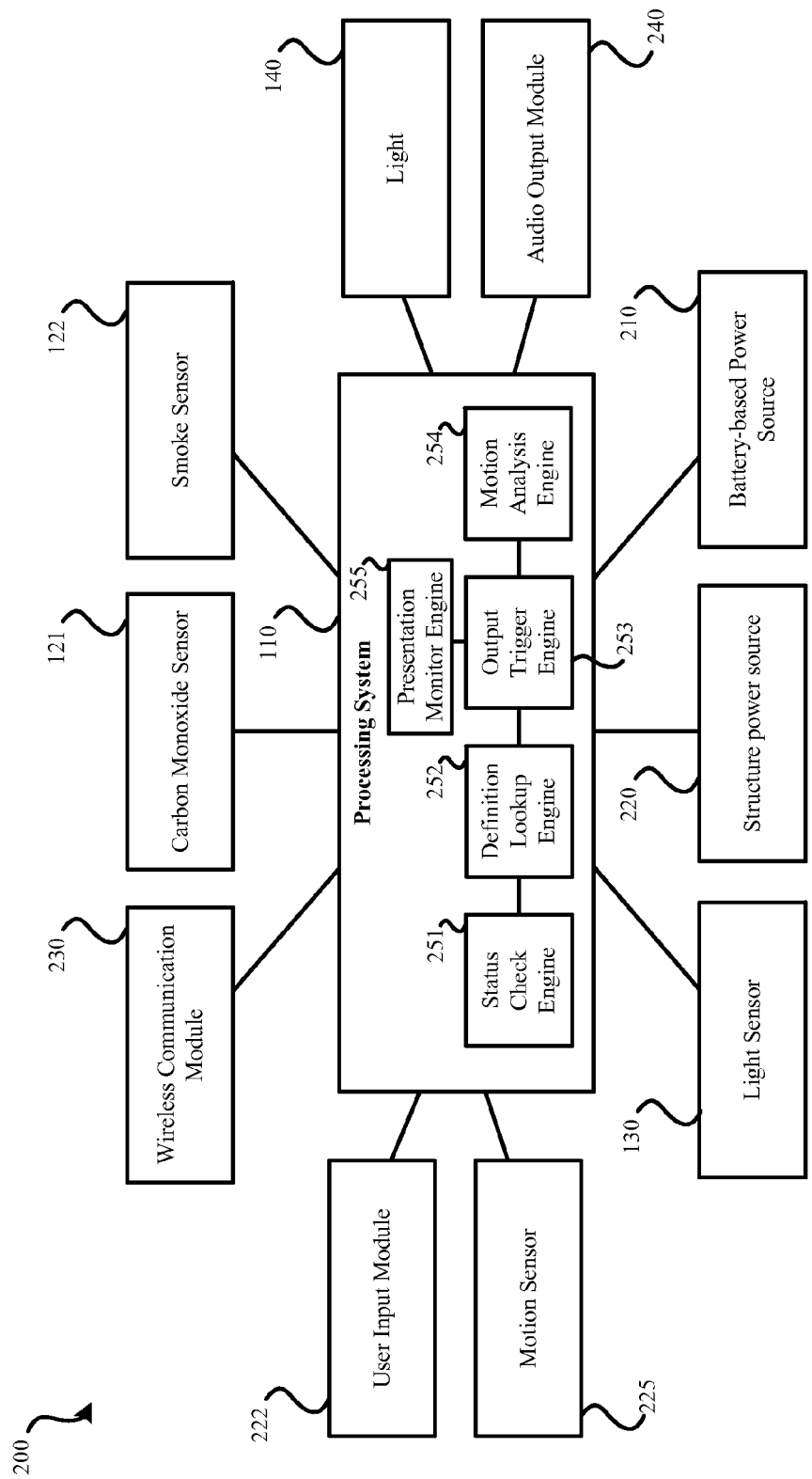
FIG. 2 illustrates another block diagram of an embodiment of a hazard detector.

FIG. 2 illustrates another block diagram of an embodiment of a hazard detector 200. Hazard detector 200 may represent a more detailed embodiment of hazard detector 100. Hazard detector 200 may include: processing system 110, carbon monoxide sensor 121, smoke sensor 122, light sensor 130, light 140, battery-based power source 210, user input module 222, structure power source 220, motion sensor 225, wireless communication module 230, and audio output module 240.

While hazard detector 100 was illustrated as having a single hazard sensor 120, hazard detector 200 has two hazard detectors: carbon monoxide sensor 121 and smoke sensor 122. To be clear, carbon monoxide sensor 121 may be configured to detect carbon monoxide and smoke sensor 122 may be configured to detect smoke. In some embodiments, multiple forms of smoke sensors are present, including an ionization sensor and a photoelectric sensor. Both carbon monoxide sensor 121 and smoke sensor 122 may provide an indication of a presence of the hazard to processing system 110.

Light sensor 130 and light 140 may function as detailed in relation to hazard detector 100.

Hazard detector 200 is illustrated as including battery-based power source 210 and structure power source 220. In some embodiments of hazard detector 200, such a configuration may be present. Structure power source 220 may be used to power hazard detector 200 when such power is present. Structure power source 220 may represent a hardwired connector within a structure (e.g., house, building, office, etc.) configured to provide an AC or DC voltage source to one or more hazard detectors located throughout the structure. While the AC or DC power may be available a significant percentage of time (e.g., 99.5% of the time), it may be desirable for hazard detector 200 to continue functioning if power in the structure in which hazard detector 200 is installed is unavailable (e.g., during a power failure). As such, battery-based power source 210 may also be present. Battery-based power source 210 may include one or more batteries which are configured to power the various components of hazard detector 200 when structure power source 220 is not available. In some embodiments of hazard detector 200, structure power source 220 is not present. As such, hazard detector 200 may permanently rely on battery-based power source 210 to power components of hazard detector 200. Structure power source 220 and battery-based power source 210 are illustrated in FIG. 2 as connected with processing system 110. Processing system 110 may be configured to determine if structure power source 220 is available and/or check a charge level of battery-based power source 210. It should be understood that, while structure power source 220 and battery-based power source 210 are illustrated as only connected with processing system 110, this is for simplicity only; structure power source 220 and battery-based power source 210 may be connected to the various components of hazard detector 200 as necessary to power such components.

Motion sensor 225 may be configured to detect motion in the vicinity of hazard detector 200. Motion sensor 225 may be configured to detect one or more gestures that may be performed by user in the vicinity of hazard detector 200. In some embodiments, motion sensor 225 may be a passive infrared (PIR) sensor that detects received infrared radiation. For instance, motion sensor 225 may be configured to detect a wave gesture performed by user. In some embodiments, multiple waves may be required to be performed by the user in order for a wave gesture to be detected. In some embodiments, motion sensor 225 may only be enabled at certain times, such as to conserve power. If only battery-based power source 210 is available, motion sensor 225 may only be enabled for a predefined period of time after a status is output via light 140 to a user. As such, motion sensor 225 may be used to detect if a gesture is performed by the user within a predefined amount of time after the status has been output via light 140. If structure power source 220 is available, motion sensor 225 may be enabled a greater amount of time. For instance, motion sensor 225 may be used to monitor for whenever a user is within the vicinity of hazard detector 200. Such motion detection may be used to enable lighting to allow a user to see in the vicinity of hazard detector 200 and/or may be used to control and/or provide data to HVAC systems within the structure. If structure power source 220 is available, motion sensor 225 may, in some embodiments, only be enabled for a predefined period of time after status has been presented via light 140 in order to monitor for a gesture performed by a user in the vicinity of hazard detector 200.

User input module 222 may represent an alternate form of input component through which a user can provide input to processing system 110 in addition or in alternate to a gesture. User input module 222 may take the form of a button or switch on hazard detector 200. By depressing the button or actuating the switch, a user can provide input via user input module 222 to processing system 110. For instance, user input module 222 may be used to disable the alarm currently sounding by hazard detector 200.

Wireless communication module 230 may be configured to allow processing system 110 to communicate with a wireless network present within the structure in which hazard detector 200 is installed. For instance, wireless communication module 230 may be configured to communicate with a wireless network that uses the 802.11a/b/g network protocol for communication. Wireless communication module 230 may permit processing system 110 to communicate with a remote server. The remote server may be configured to provide information to processing system 110 about an account of the user associated with hazard detector 200. For instance, if an account of the user maintained at the remote server requires attention from a user, such indication may be provided to processing system 110 via wireless communication module 230. Such indication may be provided by the remote server in response to inquiry from processing system 110 made to the remote server. Further, processing system 110 may transmit status information to a remote server. Such an arrangement may permit a user to view status information by logging in to the remote server via a computing device.

Audio output module 240 may be configured to output various forms of audio in response to data provided to audio output module 240 by processing system 110. Audio output module 240 may be a speaker that can output recorded or synthesized spoken messages. For instance, voice-based messages, which may indicate the presence of a hazard or may provide detail on the status of the hazard detector 200, may be output by audio output module 240 in order to be heard by a user in the vicinity of hazard detector 200. Audio output module 240 may be configured to output an alarm sound, such as a shrill beep or tone that is intended to alert users to the presence of a hazard. Different patterns and/or tones of sound may be used to alert users to different types of hazards. In some embodiments, spoken messages may be interspersed with patterns and/or tones of sound to alert users to the presence of a hazard.

Processing system 110, which may be configured to communicate with the various components presented in FIG. 2, is part of hazard detector 200. For instance, processing system 110 may receive data from motion sensor 225, user input module 222, wireless communication module 230, carbon monoxide sensor 121, smoke sensor 122, battery-based power source 210, structure power source 220, and/or light sensor 130. Processing system 110 may also output data to various components of hazard detector 200, including wireless communication module 230, light 140, and/or audio output module 240. Processing system 110 may be configured to periodically perform, or, in response to environmental condition, perform a status check of one or more components of hazard detector 200. For instance, processing system 110 may be configured to check a charge level of battery-based power source 210, check whether structure power source 220 is available, determine account status maintained at a remote server via wireless communication module 230, and/or test whether sensors, such as carbon monoxide sensor 121 and/or smoke sensor 122, are functional. Processing system 110 may then output information regarding the status to a user via light 140 and/or audio output module 240. It should be understood that processing system 110 may be configured to perform various blocks of the methods detailed in relation to FIGS. 17-21.

Processing system 110 may contain multiple engines that are implemented using software (running on hardware), firmware, and/or hardware. Such engines may include status check engine 251, definition lookup engine 252, output trigger engine 253, motion analysis engine 254, and presentation monitor engine 255. It should be understood that such engines may be split into a greater number of engines or may be combined into fewer engines. Status check engine 251 may be configured to perform a status check periodically, such as once per day or once per hour. In some embodiments, status check engine 251 may be configured to perform a status check based on an indication from output trigger engine 253 that indicates that a status indication is to be output. Status check engine 251 may check the status of one or more components of the hazard detector. Status check engine 251 may check the status of: a battery level of battery-based power source 210 as compared to one or more thresholds, carbon monoxide sensor 121 (e.g., functional, nonfunctional expired, etc.), smoke sensor 122 (e.g., functional, nonfunctional expired, etc.), motion sensor 225 (e.g., functional, nonfunctional), structure power source 220 (e.g., available, unavailable), light sensor 130 (e.g., functional, nonfunctional), etc. Status check engine 251 may check the status of a user account associated with the hazard detector by querying a remote server. Status check engine 251 may check battery-based power source 210 against multiple thresholds. A first threshold, which may be greater than the second threshold, may be used to determine that a battery is approaching a low voltage and the user should consider replacing it. The second threshold may be used to determine the battery's voltage is low and should be replaced immediately. More than two thresholds are also possible for assessing battery voltage.

Based on the result of the status check by status check engine 251, an output may be supplied to definition lookup engine 252. Definition lookup engine 252 may determine a color, animation, and/or speed at which light 140 should be illuminated to provide an indication of the status to one or more users. Definition lookup engine 252 may access one or more lookup tables to determine an appropriate combination of color, animation, and/or speed for representing the determined status.

Output trigger engine 253 may cause the appropriate combination of color, animation, and/or speed selected by definition lookup engine 252 to be used to illuminate light 140 in response to a determination that data from light sensor 130 is indication of the light in the ambient environment of hazard detector 200 being at or below a stored threshold brightness level and/or that at least an amount of time has elapsed since the previous time that an indication of the status was output. Presentation monitor engine 255 may determine whether at least a stored threshold period of time has elapsed since the last time an indication of the status of the hazard detector was output. If the threshold period of time has not elapsed, presentation monitor engine 255 may provide an indication to output trigger engine 253 that prevents light 140 from being illuminated based on the status.

Motion analysis engine 254 may be active during and/or following presentation of the status via light 140 (for up to a stored threshold period of time). If a particular gesture, such as a wave gesture is identified by motion analysis engine based on data from motion sensor 225, detail about the status may be output via audio output module 240 or some other component of hazard detector 200.

Figure 3:
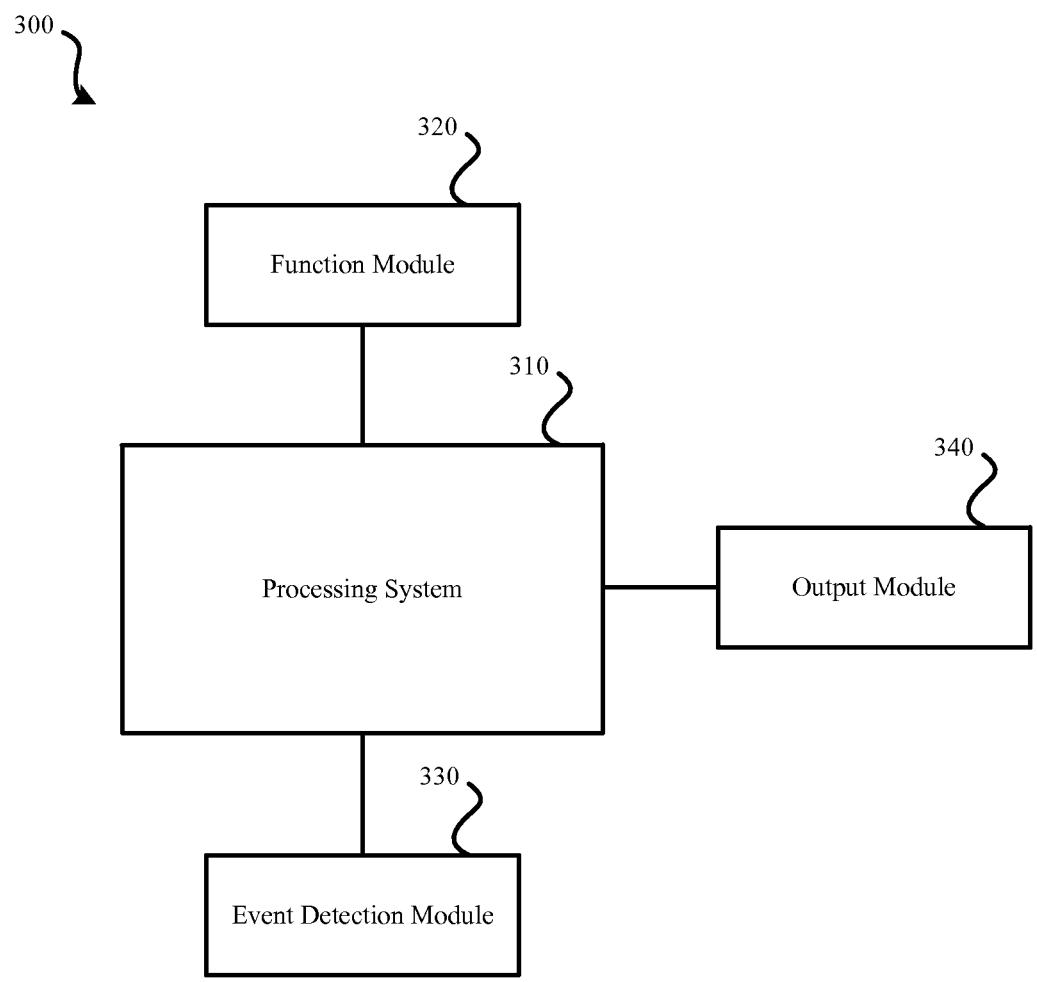
FIG. 3 illustrates a block diagram of a system that may perform a function in response to an unrelated event.

While the previous detailed embodiments are focused on hazard detectors configured to detect hazards, such as fire, smoke, or carbon monoxide in the environment of the hazard detector, embodiments detailed in this document may be adapted to detection of other forms of events. FIG. 3 illustrates a block diagram of a system 300 that may perform a function in response to an unrelated event. System 300 may be configured to detect one or more forms of events. Such event may or may not qualify as a hazard. System 300 may represent embodiments of hazard detector 100 and/or hazard detector 200 of FIGS. 1 and 2, respectively. Alternatively, system 300 may include: processing system 310, function module 320, event detection module 330, and output module 340.

Function module 320 may be configured to perform some function, such as monitoring an environment in the vicinity of system 300 for one or more conditions. For example, these conditions may be hazards. However, it should be understood that one or more conditions being monitored for by function module 320 may be other than hazards. As an example, function module 320 may monitor for motion, temperature, humidity, and/or the presence or absence of some other condition or object. Function module 320 may perform some function other than a monitoring function. For instance, function module 320 may perform a status check of some other system or may serve to activate some other component or system. Function module 320 may perform any number of various functions such as control of a motor, a pump, a medical system, a computing device, etc. Function module 320 may provide input to processing system 310. Further, processing system 310 may be configured to check a status of function module 320.

Event detection module 330 may be configured to monitor the vicinity of system 300 for one or more types of event. This event may trigger one or more actions to be performed by processing system 310. For example, a triggering event detected by event detection module 330 may cause processing system 310 to initiate function module 320 and/or perform a status check of one or more components of system 300, such as function module 320. The event detected by event detection module 330 may be unrelated to the functioning of function module 320. While event detection module 330 may be configured to detect an event that coincides with the time at which the user is likely to desire information about system 300, this event may be unrelated to performance of any other function of system 300. For example, if function module 320 is monitoring humidity, event detection module 330 may be configured to trigger based on brightness in the environment of system 300 or some other condition, such as temperature, the presence of a chemical or other substance in the air, motion, or some other type of event or condition. As a simple example, if event detection module 330 is configured to monitor for brightness in the vicinity of system 300, when the brightness level in the vicinity of system 300 reaches a predefined value, processing system 310 may perform a self-test or status check on one or more components of system 300, such as function module 320 and/or an onboard power source, such as a battery. Output module 340 may be used to provide an output that indicates the result of the self-test or status check. In some embodiments, rather than the self-test or status check being performed in response to the event detected by event detection module 330, the self-test or status check may be performed based on some other schedule, but an indication of the results of the self-test or status check may be output via output module 340 in response to the events being detected by event detection module 330.

Event detection module 330 may be configured to detect an event that coincides with the time at which the user is likely to desire information about system 300. One possible example is based on brightness of light in the ambient environment of system 300. For instance, when the light within the vicinity of system 300 increases, it may correspond to a light being turned on and the user entering a room in which system 300 is present. Similarly, when brightness within the vicinity of system 300 decreases, it may correspond to a light being turned off and the user leaving a room in which system 300 is present. Both of these events may represent an opportune time for either a status check to be performed or results of a status check to be output to a user. For instance, if function module 320 is monitoring a condition in a room of a structure, upon entering the room and turning on a light, a user may find it useful to learn the status of system 300. Similarly, in certain circumstances, the user may find it useful to learn the status of system 300 upon leaving the room of the structure in which system 300 is installed.

Output module 340 may be configured to provide an indication of the self-test or status check performed by processing system 310. Output module 340 may include components configured to visually output an indication of the status or self-test and/or may include components configured to output audio such that an auditory indication of the status or self-test is output. For instance, output module 340 may include one or more speakers and/or one or more lights, such as LEDs, such as detailed in relation to hazard detectors 100 and 200. Output module 340 may receive data from processing system 310 which triggers sound and/or visual output. In some embodiments, processing system 310 may output spoken messages to be output by output module 340. It should be understood that embodiments of system 300 may be further configured to include components such as those detailed in relation to hazard detector 200 of FIG. 2.

Figure 4:
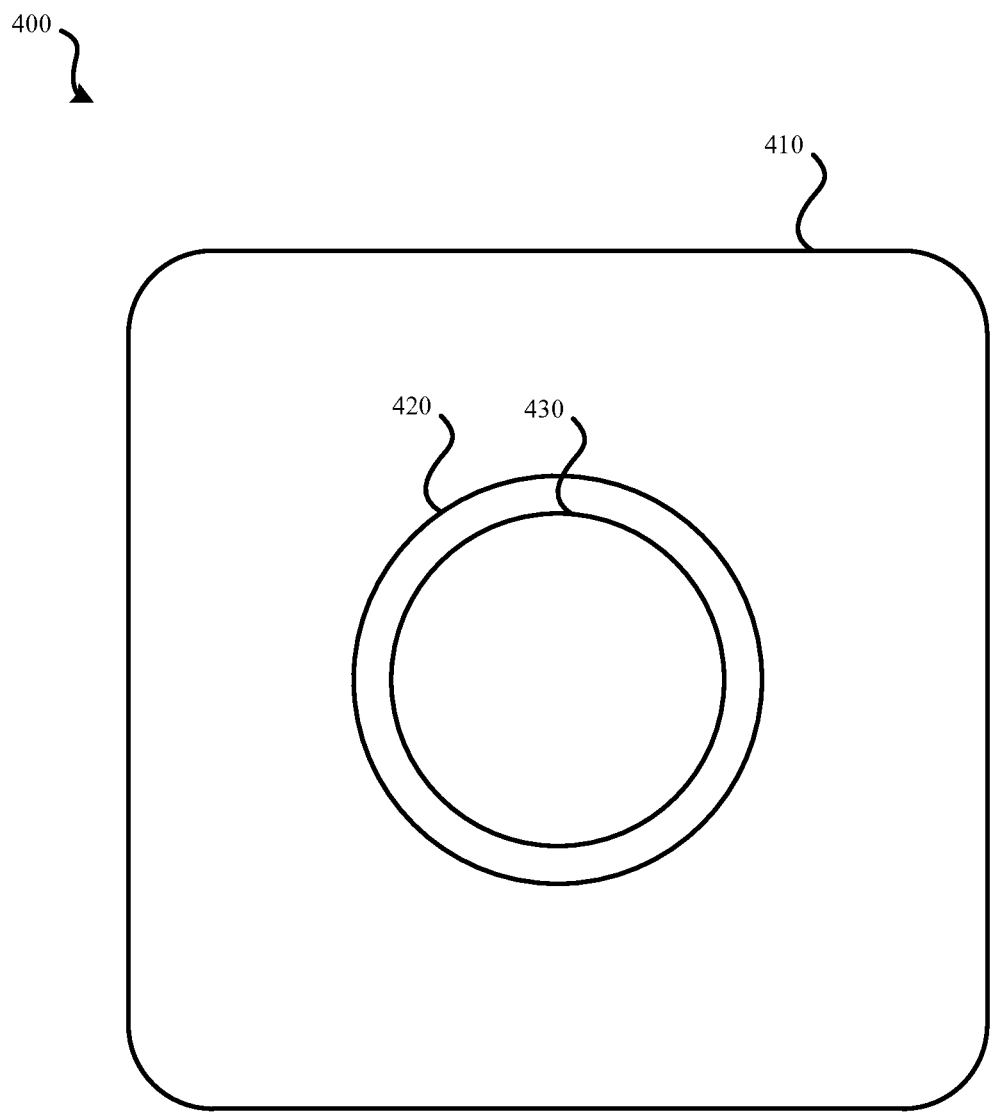
FIG. 4 illustrates an external view of an embodiment of a hazard detector.

FIG. 4 illustrates an external view of an embodiment of a hazard detector 400. Hazard detector 400 may represent hazard detector 100, hazard detector 200, or system 300 of FIGS. 1-3, respectively. Hazard detector 400 may include case 410, light 420, and/or center region 430. Case 410 may represent a shell of hazard detector 400 which is configured to be mounted to a wall or ceiling. Case 410 may be configured to allow airflow through hazard detector 400 to permit one or more sensors within hazard detector 400 to be exposed to the air of the ambient environment of hazard detector 400. On the side of case 410 opposite the side used for mounting, light 420 may be present. Light 420 may include one or more light sources, such as LEDs. Light 420 may be configured to present various colors and/or various lighting patterns, possibly with such patterns presented at various speeds. For instance light 420 may be configured to present lighting patterns that appear to produce a circulation effect, flash, and/or fade. While light 420 may be used to confer information about a status of hazard detector 400, light 420 may also be used to provide ambient lighting. For instance, a color unassociated with a status may be output by light 420 when motion is detected by hazard detector 400 and the ambient lighting is determined to be less than a threshold value. Further, in some embodiments, hazard detector 400 may determine whether such a feature has been enabled or disabled by user and/or if hazard detector 400 is installed in a bedroom (e.g., by determining whether a user has classified hazard detector 400 as installed within a bedroom).

While light 420 is illustrated as a circle (or halo), it should be understood that, in other embodiments of hazard detector 400, other shapes may be used for light 420. For instance, light 420 may be elliptical, square, triangular, some other geometric shape, some other abstract shape, or a line. Similarly, in some embodiments, case 410 is square or rectangular, with rounded edges. While such a design may be pleasing to the eye, other shapes, both geometric or abstract, may be used to house the functional components of hazard detector 400. In some embodiments, light 420 represents a depressed portion of case 410 which reflects light generated within hazard detector 400. For instance, one or more LEDs may be located within case 410, such as behind center region 430 and may be output light that reflects off a depressed portion of case 410 in the shape of light 420.

Center region 430 may include a lens that is used in conjunction with a motion sensor to determine if a user is present and/or detect whether a gesture has been performed by user. Center region 430 may serve a dual function: functioning as a lens and as a button which can be pushed by user to provide input to hazard detector 400. In some embodiments, center region 430 is only a button. When center region 430 is a button, by having center region 430 encircled by light 420, it may be easy for a user to locate the button in a darkened environment when light 420 is illuminated. In such a situation, the user would only need to push within the circle of light or other region defined by light 420 in order to actuate the button.

Figure 5:
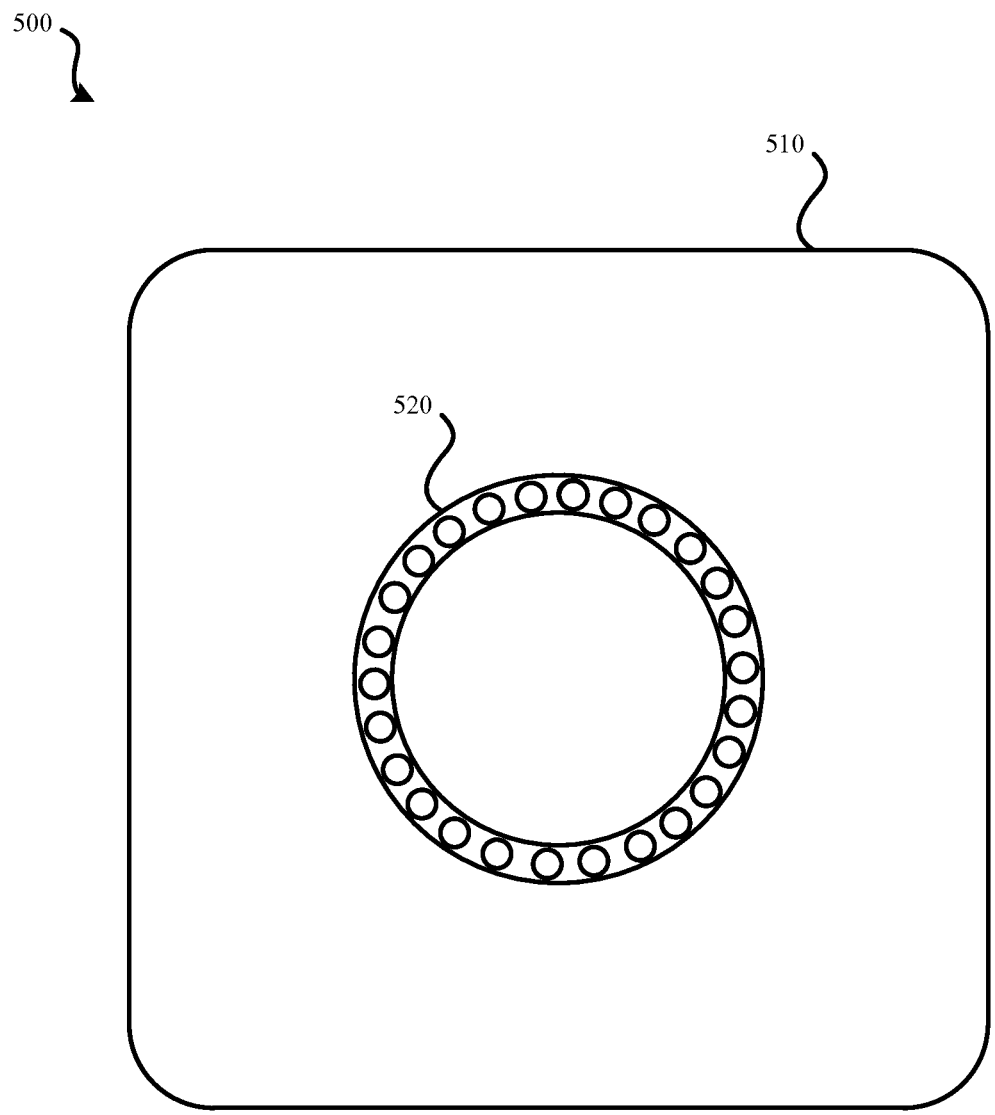
FIG. 5 illustrates an external view of an embodiment of a hazard detector that uses multiple light emitting diodes (LEDs) as a light.

FIG. 5 illustrates an external view of an embodiment of a hazard detector 500 that uses multiple lighting elements as part of a light. In hazard detector 500, multiple LEDs are used as the lighting elements as part of light 520. Hazard detector 500 may represent an embodiment of hazard detector 400 of FIG. 4. Hazard detector 500 may include hazard detector 100, hazard detector 200, or system 300 of FIGS. 1-3, respectively. Light 520 may include multiple LEDs. In FIG. 5, light 520 is made up of 26 LEDs. It should be understood that the number of LEDs illustrated in FIG. 5 is merely exemplary. For instance, a fewer or a greater number of LEDs may be used to create light 520. As a specific example, five LEDs may be used as part of light 520. By using multiple LEDs, various lighting effects may be created in which only portions of light 520 are illuminated at a given time and/or various portions of light 520 are illuminated with different colors and/or different brightness levels at a given time. As an example, the LEDs of light 520 may fade from not producing light to a defined brightness level, then, either immediately or after a defined time period, fade back to not producing light.

In some embodiments, LEDs may be used as part of light 520, which is present on case 510. In other embodiments, other forms of components that create visible light may be used in place of LEDs, such as light sources that use fluorescent or incandescent technologies. Further, light 520 is illustrated in FIG. 5 as being arranged in a circle. It should be understood that in other embodiments, light 520 may be arranged in other shapes, such as an oval, square, rectangle, line, or some abstract shape.

Figure 6:
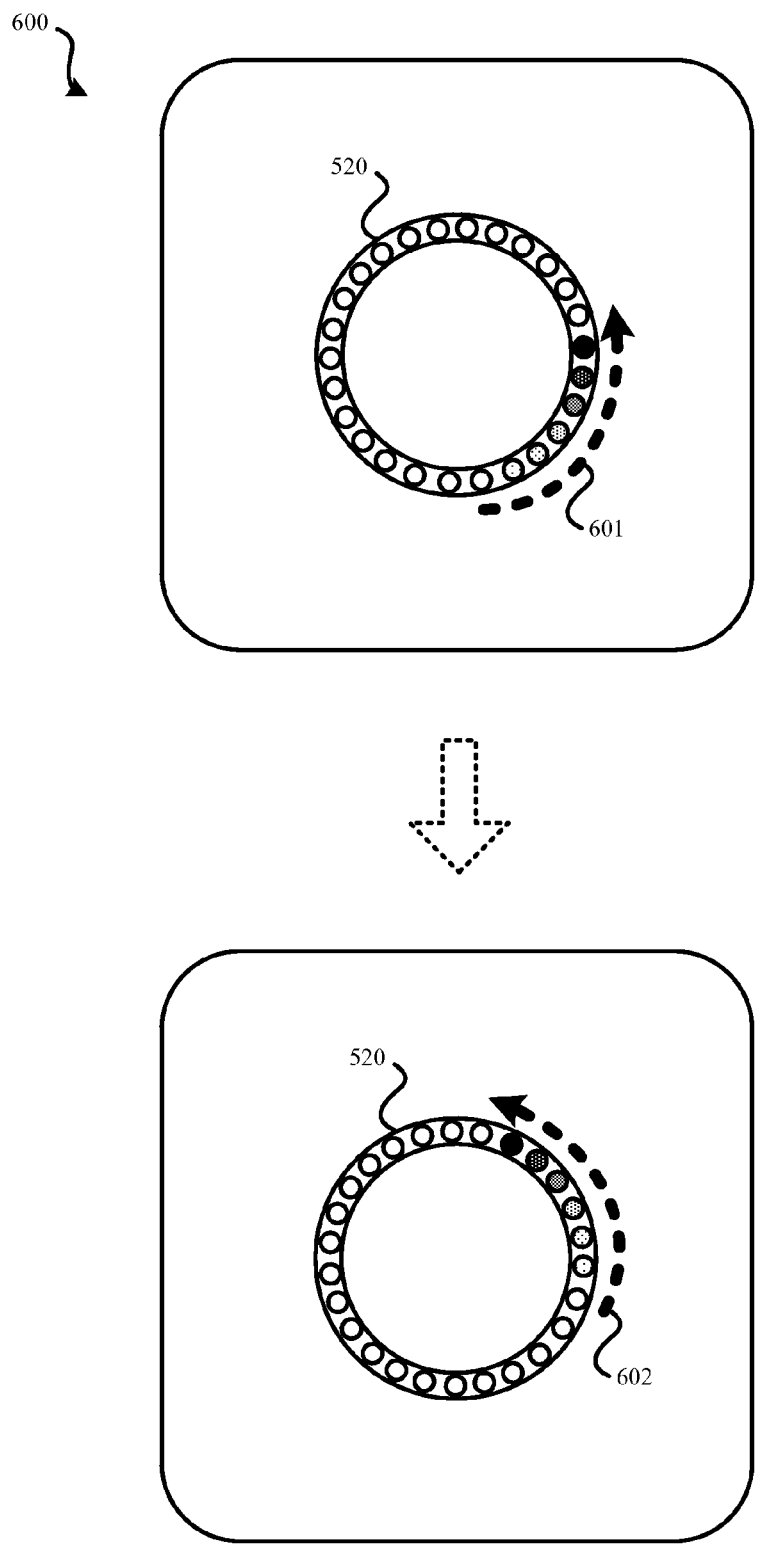
FIG. 6 illustrates an external view of an embodiment of a hazard detector that outputs a circular pattern of light.

FIG. 6 illustrates an external view of an embodiment of a hazard detector that outputs a circular pattern of light. Hazard detector 600, which is illustrated in FIG. 6 in two states, may represent hazard detector 500 of FIG. 5 and/or hazard detector 400 of FIG. 4. Hazard detector 600 may include hazard detector 100, hazard detector 200, or system 300 of FIGS. 1-3, respectively. FIG. 6 illustrates hazard detector 600 outputting a lighting effect. This lighting effect is output in a (roughly) circular pattern and can be referred to as a circulation effect or halo effect.

The circulation effect, also referred to as a halo-sweep effect, can be caused by various lighting elements, such as LEDs, of light 520 being illuminated at different brightness levels at a given time. Lighting elements of light 520 are illuminated consecutively, then faded to off. This effect results in the appearance of a point of light spinning around light 520 with a tail. A user viewing hazard detector 600 may view the circulation or halo effect and understand the status of the hazard detector based on the lighting effect and/or the color of light being output by light 520. In some embodiments, when the circulation effect is being output, each lighting element of light 520 may output the same color, or multiple colors may be output by different lighting elements. Imaginary arrow 601 illustrates the circulation effect, the opposite direction is also possible. The darker a lighting element is shaded in FIG. 6, the brighter the lighting element may be illuminated. Therefore, in some embodiments, a first lighting element may be bright, while the lighting element immediately behind it may be slightly less bright, and so on. Imaginary arrow 602 shows the circulation effect of hazard detector 600 at a later time at which a different lighting element is now the brightest lighting element with subsequent lighting elements being illuminated progressively less bright.

Figure 7:
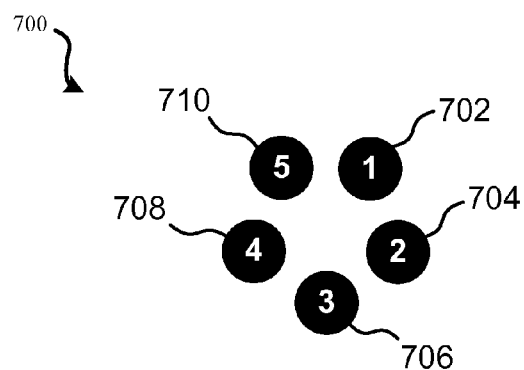
FIG. 7 illustrates an embodiment of a hazard detector having LEDs arranged in a circle.

FIG. 7 illustrates an embodiment of lighting elements 700 arranged in a circle. Such a pattern of lighting elements (e.g., LED lights) may be coupled on a circumferentially arranged ring portion of a hazard detector. Such a pattern can include five lighting elements: lighting elements 702, 704, 706, 708 and 710. Lighting elements 700 may be turned on and off according to a number of patterns and each may cycle through different hue ranges. The color of each of the lighting elements may also vary in order to provide an additional variety of visual effects. While five lighting elements are illustrated, it should be understood that a fewer or a greater number of lighting elements may be incorporated as a light of a hazard detector or some other form of device.

Figure 8A:
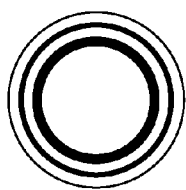
FIGS. 8A-8D illustrate an embodiment of four various visual effects that may be generated using a light of a hazard detector.

FIGS. 8A-8D illustrate an embodiment of four visual effects (also referred to as animations) that may be generated using a light of a hazard detector. FIG. 8A illustrates a representation of a pulsing effect that may be created when all of lighting elements 702, 704, 706, 708 and 710 (shown in FIG. 7) are turned on and off simultaneously. Alternatively, all of lighting elements 702, 704, 706, 708 and 710 may increase and decrease the brightness of the light they each produce in a synchronized fashion to create a pulsing effect.

Figure 8B:
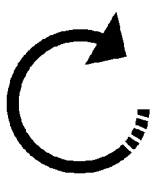
Figure 10:
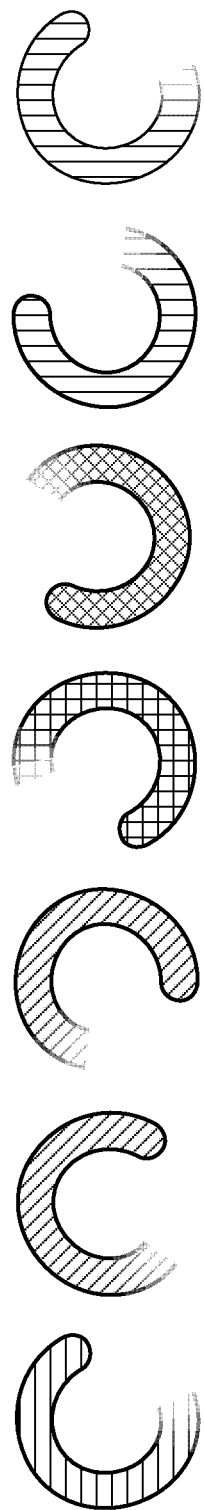
FIG. 10 illustrates another embodiment of a rotating visual effect that may be output by a hazard detector.

FIG. 8B illustrates a representation of a rotating effect (also referred to as a circulation effect or halo sweep effect) that may be created when all of lighting elements 702, 704, 706, 708 and 710 are turned on and off sequentially in a clockwise direction to create a rotating effect. Furthermore, turning on and off the lights may be done in a gradual fashion. For example, lighting element 704 may gradually turn off and lighting element 702 gradually turns on while lighting elements 706, 708 and 710 are turned on at an equal brightness. FIG. 10 provides a further illustration of the rotating visual effect of FIG. 8B (and FIG. 6), according to an embodiment. Viewed from left to right, FIG. 10 shows new lights turning on at one end of the rotating visual effect and other lights gradually turning off at the other end of the rotation visual effect. The hatch patterns of each of the sequential representations illustrate how the rotating light may change color during the rotation sequence. Although lighting elements 702, 704, 706, 708 and 710 may each be a different color individually, the colored light mixing causes the color of the rotating visual effect to constantly change through the course of the visual effect.

Figure 8C:

FIG. 8C illustrates a representation of a wave visual effect that may be created when lighting elements 700 (shown in FIG. 7) turn on and off in a side-to-side direction. For example, at a given point in time as shown in FIG. 8C, lighting element 710 may be most bright, lighting elements 708 and 702 may be the next brightest, and lighting elements 706 and 704 may be the least bright. Shortly thereafter, the lights may gradually change brightness in a linear manner such that lighting elements 704 and 706 are the brightest, lighting elements 708 and 702 are the next brightest, and lighting element 710 is the least bright.

Figure 8D:
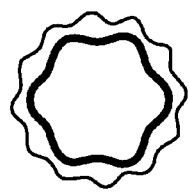
Figure 11:
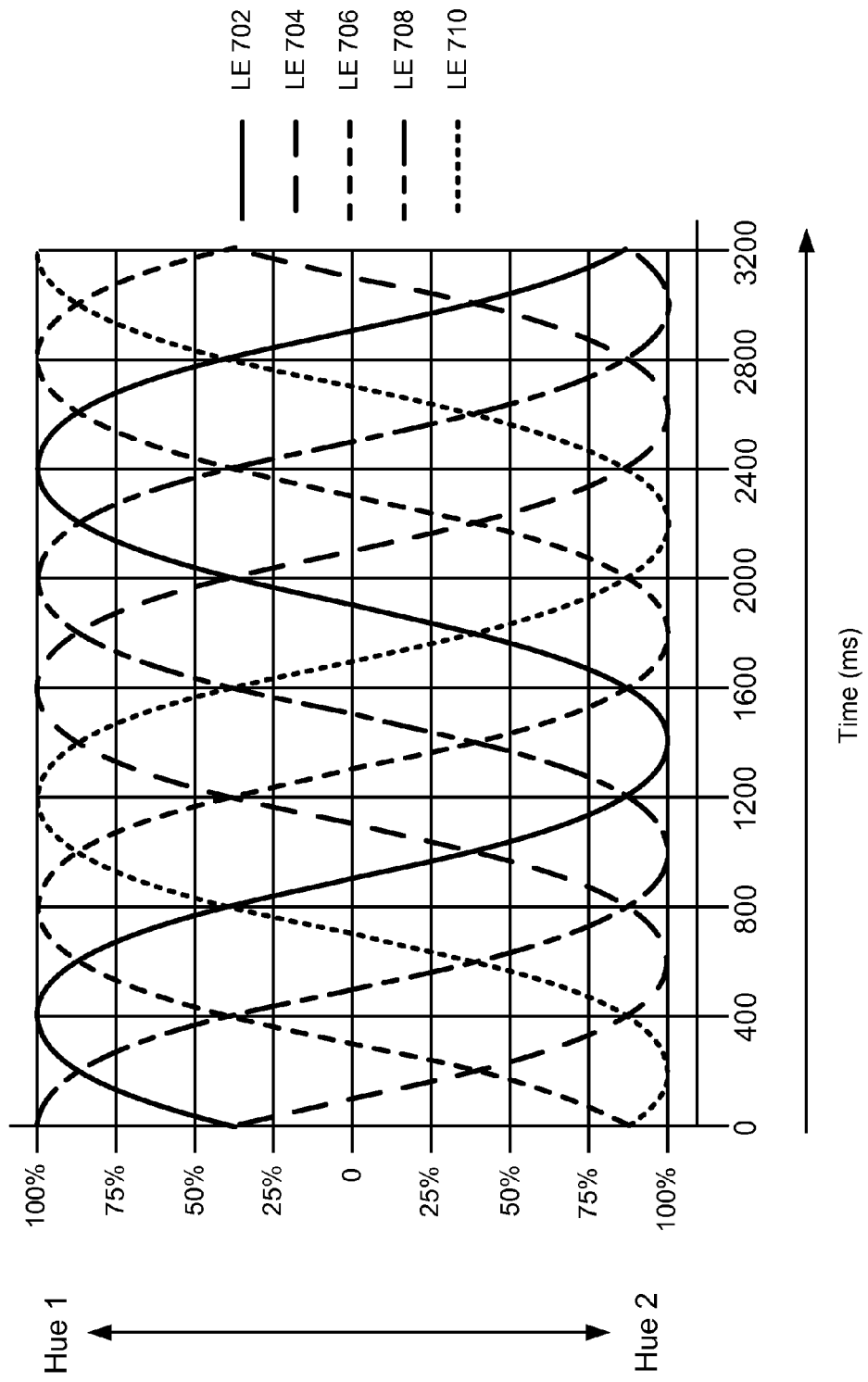
FIG. 11 illustrates an embodiment of various hue range patterns which may be used to generate visual effects by a hazard detector.

FIG. 8D illustrates a representation of a shimmer visual effect that may be created when each of the lighting elements 700 cycle through a hue range pattern with each lighting element's hue range pattern being out of sync with all of the lights. FIG. 11 illustrates the different hue range patterns associated with each of the lighting elements 700 for the shimmering visual effect, according to an embodiment. The extent to which the lighting elements 702, 704, 706, 708 and 710 are out of sync may be varied in order to produce variations of the shimmer visual effect.

Figure 9A:
FIGS. 9A and 9B illustrate an embodiment of a pulse visual effect that may be generated using a light of a hazard detector.
Figure 9B:

FIGS. 9A and 9B illustrate an embodiment of a pulse visual effect that may be generated using a light of a hazard detector. FIG. 9A represents an on and off pattern for power off or no power available situations wherein the pulse animations will transition smoothly through pulses in order to provide an alert in a non-distracting manner. FIG. 9B represents left-to-right pulse patterns that could be used when presenting a user with selectable options via visual effects. For example, a button (such as center region 430 of FIG. 4) may be used to select a language preference for the operation of hazard detector 400 during an initial setup procedure. A user could be asked to press such a button when the left side is pulsing for English and when the right side is pulsing for Chinese. Therefore, a user may wait until the side of light is pulsing or otherwise illuminated that is associated with the user's desired selection. In some embodiments, rather than pressing a button, the user may perform a gesture, such as one or multiple waves of a hand.

In various embodiments, the visual effects described above could be varied in a number of different ways. For example, each effect may be animated faster or slower, brighter or dimmer, for a specific number of animation cycles, with only some of the light participating, and using different colors, e.g., white, blue, green, yellow and red. and/or a mixture of multiple colors.

These visual effects may be generated by the hazard detectors detailed herein for a variety of specified purposes. For example, a specific color, animation, animation speed, etc. or combinations thereof may represent one or more of the following alerts or notifications provided a hazard detector: booting up, selecting language, ready for connections, connected to client, button pressed, button pressed for test, countdown to test, test under way, test completed, pre-alarms, smoke alarms, carbon monoxide alarms, heat alarms, multi-criteria alarms, hushed after alarm, post-alarm, problems, night light state, reset, shutdown begin, shutdown, safely light, battery very low, battery critical, power confirmation, and more. By way of example and not by way of limitation, FIGS. 12 and 13 illustrate an exemplary "visual vocabulary" for visual effects and colors that may be used by embodiments of hazard detectors.

FIG. 11 illustrates various hue range patterns associated with each of the lighting elements 700 for the shimmering visual effect, according to an embodiment. The extent to which lighting elements (abbreviated LE in FIG. 11) 702, 704, 706, 708 and 710 are out of sync may be varied in order to produce variations of the shimmer visual effect. As illustrated, each lighting element is increased and decreased in brightness between two hues as time progresses. Some or all of the lighting elements are "out of sync" in that the lighting elements, while illuminating according to the same pattern, do so at different times. It should be understood that the pattern illustrated in FIG. 11 could be adapted for fewer or greater numbers of lighting elements. Also, the waveforms could be altered to produce a different visual effect.

FIG. 12 illustrates an embodiment 1200 of definitions for visual effects that may be used by a hazard detector, such as the hazard detectors of FIGS. 1-6. Color definitions 1210, animation definitions 1220, and speed definitions 1230 may be stored by a hazard detector or may be accessible by the hazard detector from some remote location, such as a cloud-based server (e.g., cloud-computing system 1564). Such definitions of colors, animations, and/or speeds may be provided to a user, such as in the form of a quick reference sheet or manual provided with a hazard detector when purchased. As such, a user can learn or look-up the meaning of a particular visual effect. Each color, animation, and speed may have an individualized meaning. For instance, the speed of an animation may be used to indicate a level of urgency. Animation may be used to provide an acknowledgment ("OK"), an indication that attention is needed, and/or some other status. Such an animation used in conjunction with a speed may alert the user as to how urgent the status associated with the animation is. Further, various colors may be incorporated to provide more information to a user, such as green for "OK", yellow for "something may be wrong" or a warning, and red for "something is definitely wrong." Other colors may be used for other forms of messages. Further, a separate color, such as white, may be used by the light for ambient lighting provided by the hazard detector in certain situations as previously detailed. As an example, if a battery is low but does not yet need to be replaced, the color may be yellow ("something may be wrong"), the animation may be "here's my status", and the speed may be slow. If the battery is not replaced, the speed may transition to fast after a time. Once the battery must be replaced, the color may be red ("something is definitely wrong"), the animation may be a circulation ("I need your attention") and the speed may be fast (or alarm). As such, a battery may be checked against multiple voltage thresholds—the lower the voltage, the more urgent the presented status.

In some embodiments, color definitions 1210, animation definitions 1220, and speed definitions 1230 may be used independently to select a color, animation, and speed by the hazard detector based on a status check of the hazard detector. A look-up may be performed using color definitions 1210, animation definitions 1220, and speed definitions 1230 to select a color, animation, and speed that corresponds to the status determined by the hazard detector. The color, animation, and/or speed selected from color definitions 1210, animation definitions 1220, and/or speed definitions 1230 may be used by the hazard detector to output a status via a light of the hazard detector.

FIG. 13 illustrates an embodiment 1300 various combinations of visual effects (also referred to as animations) and color that may be used by a hazard detector, such as the hazard detectors of FIGS. 1-6. Such combinations may be stored in the form of a look-up table by a hazard detector or may be accessible via a network from a remote computerized device, such as a cloud-based server system (e.g., cloud-computing system 1564). Once a status is determined by the hazard detector, a table such as presented in embodiment 1300 may be used to determine an animation, color, and/or speed to use for outputting an indication of the status. Color 1301 may be red, color 1302 may be yellow, color 1303 may be green, color 1304 may be blue, and color 1305 may be white. Other color assignments are also possible. Definitions of colors, visual effects, and/or speeds may be stored by a hazard detector. In response to a condition determined by the hazard detector during a status check, the processing system of the hazard detector may look up or otherwise determine the appropriate combination of colors, visual effect, and/or speed to use to illuminate the light. The light may then be illuminated according to the determined combination to convey information to one or more users. Again here, definitions of colors and animations may be provided to a user, such as in the form of a quick reference sheet or manual provided with a hazard detector when purchased.

Figure 14:
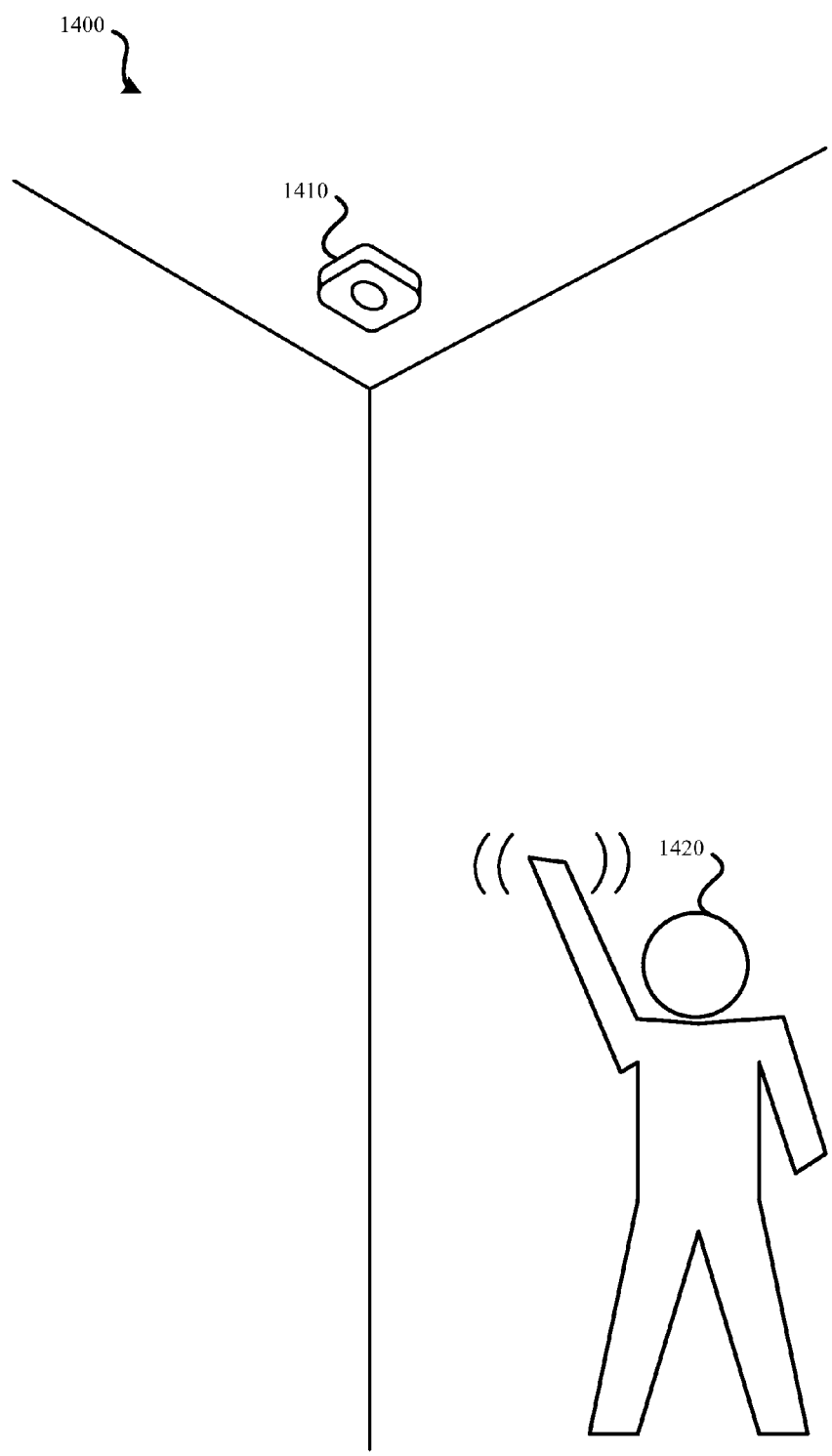
FIG. 14 illustrates an embodiment of a user performing a gesture that is detected by a hazard detector.

FIG. 14 illustrates an embodiment 1400 of a user performing a gesture that is detected by a hazard detector. User 1420 is performing a gesture of waving his hand in order to provide input to hazard detector 1410. Hazard detector 1410 may represent one of the previously detailed hazard detectors, such as those detailed in relation to FIGS. 1 through 6. The wave gesture being performed by user 1420 may consist of a single wave or multiple waves of the user's hand. While illustrated embodiment 1400 focuses on a wave gesture, it should be understood that other forms of gestures may be performed by user 1420 and detected by hazard detector 1410. Hazard detector 1410 may monitor for a gesture being performed by user 1420 for a predefined amount of time after information has been presented by a light of hazard detector 1410. For instance, if a light of hazard detector 1410 has just presented status, for a predefined period of time, such as 10 seconds, hazard detector 1410 may monitor for a gesture being performed by user 1420. If a gesture is detected within this predefined period of time, detail about the status presented by the light of hazard detector 1410 may be provided. While the status was initially presented using the light, the further detail about the status may be presented using auditory information. For instance, a spoken message may be played aloud by hazard detector 1410. As an example, if hazard detector 1410 outputs via the light a green pulsing status update and user 1420 performs a wave gesture, a spoken message may be output by hazard detector 1410 saying "All components are functioning normally." As another example, if hazard detector 1410 outputs via the light a yellow pulsing status update and user 1420 performs a wave gesture, a spoken message may be output by hazard detector 1410 saying "The battery is low. Please replace the battery at your earliest convenience."

As can be seen in embodiment 1400, it may be difficult for user 1420 to physically reach hazard detector 1410. As such, for user 1420 to efficiently provide input to hazard detector 1410, a gesture may be preferable to allow a user to provide input without having to physically contact hazard detector 1410. Hazard detector 1410 may have a lens that targets motion detection to a conical region beneath hazard detector 1410. Such targeting of gesture and motion detection may be preferable to avoid stray motions being interpreted as a gesture.

Figure 15:
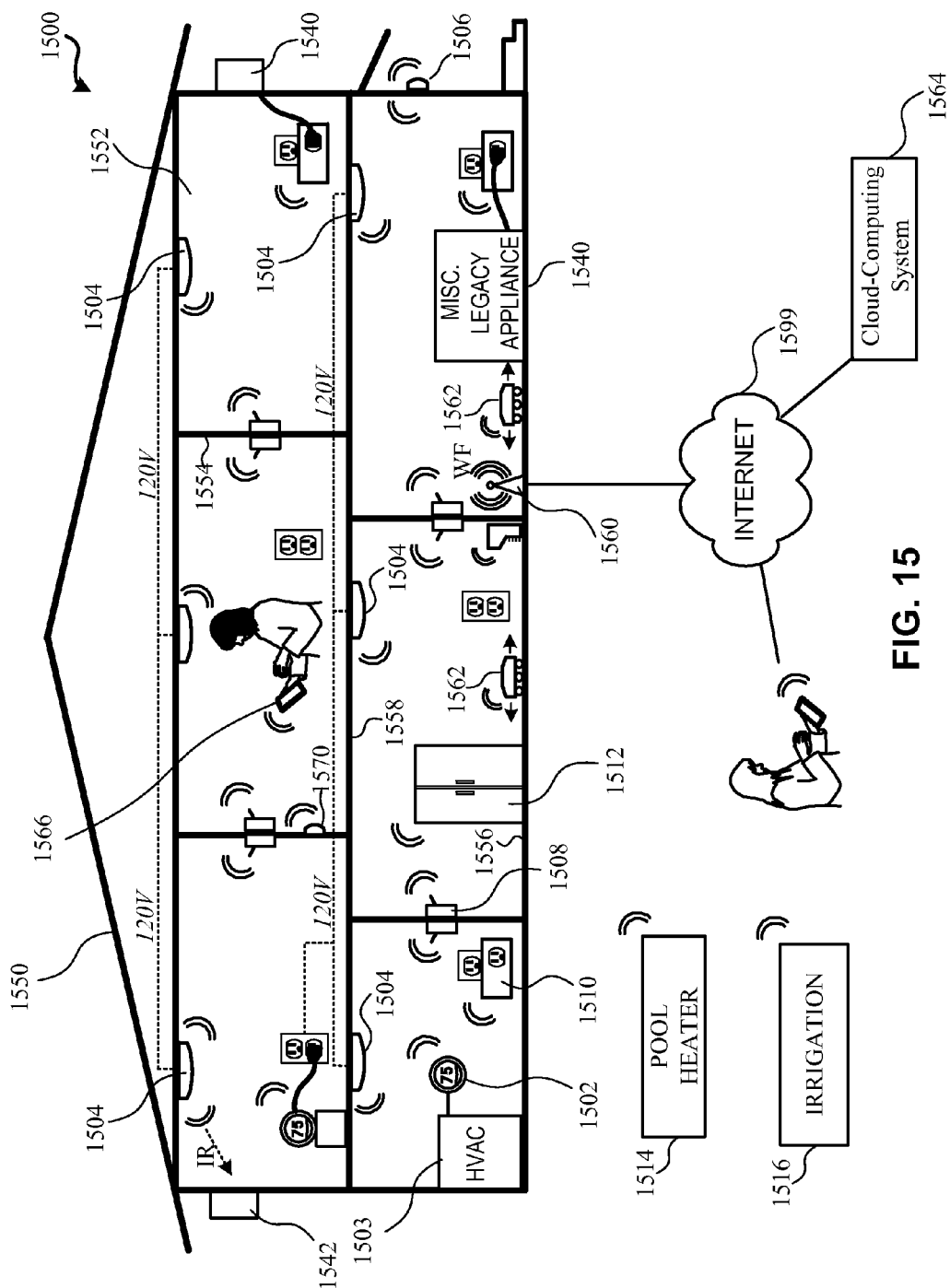
FIG. 15 illustrates an embodiment of a smart-home environment within which one or more of the devices, methods, systems, services, and/or computer program products described herein may be applicable.

Hazard detectors (and other devices), as detailed herein, may be installed in a smart-home environment. FIG. 15 illustrates an example of a smart-home environment 1500 within which one or more of the devices, methods, systems, services, and/or computer program products described further herein can be applicable, such as the hazard detectors detailed in relation to FIGS. 1-6. The depicted smart-home environment 1500 includes a structure 1550, which can include, e.g., a house, office building, garage, or mobile home. It will be appreciated that devices can also be integrated into a smart-home environment 1500 that does not include an entire structure 1550, such as an apartment, condominium, or office space. Further, the smart home environment can control and/or be coupled to devices outside of the actual structure 1550. Indeed, several devices in the smart home environment need not physically be within the structure 1550 at all. For example, a device controlling a pool heater or irrigation system can be located outside of the structure 1550.

The depicted structure 1550 includes a plurality of rooms 1552, separated at least partly from each other via walls 1554. The walls 1554 can include interior walls or exterior walls. Each room can further include a floor 1556 and a ceiling 1558. Devices can be mounted on, integrated with and/or supported by a wall 1554, floor 1556 or ceiling 1558.

In some embodiments, the smart-home environment 1500 of FIG. 15 includes a plurality of devices, including intelligent, multi-sensing, network-connected devices, that can integrate seamlessly with each other and/or with a central server or a cloud-computing system to provide any of a variety of useful smart-home objectives. The smart-home environment 1500 may include one or more intelligent, multi-sensing, network-connected thermostats 1502 (hereinafter referred to as "smart thermostats 1502"), one or more intelligent, network-connected, hazard detectors 1504, and one or more intelligent, multi-sensing, network-connected entryway interface devices 1506 (hereinafter referred to as "smart doorbells 1506"). According to embodiments, the smart thermostat 1502 detects ambient climate characteristics (e.g., temperature and/or humidity) and controls a HVAC system 1503 accordingly. The hazard detector 1504 may detect the presence of a hazardous substance or a substance indicative of a hazardous substance (e.g., smoke, fire, or carbon monoxide). The smart doorbell 1506 may detect a person's approach to or departure from a location (e.g., an outer door), control doorbell functionality, announce a person's approach or departure via audio or visual means, or control settings on a security system (e.g., to activate or deactivate the security system when occupants go and come).

In some embodiments, the smart-home environment 1500 of FIG. 15 further includes one or more intelligent, multi-sensing, network-connected wall switches 1508 (hereinafter referred to as "smart wall switches 1508"), along with one or more intelligent, multi-sensing, network-connected wall plug interfaces 1510 (hereinafter referred to as "smart wall plugs 1510"). The smart wall switches 1508 may detect ambient lighting conditions, detect room-occupancy states, and control a power and/or dim state of one or more lights. In some instances, smart wall switches 1508 may also control a power state or speed of a fan, such as a ceiling fan. The smart wall plugs 1510 may detect occupancy of a room or enclosure and control supply of power to one or more wall plugs (e.g., such that power is not supplied to the plug if nobody is at home).

Still further, in some embodiments, the smart-home environment 1500 of FIG. 15 includes a plurality of intelligent, multi-sensing, network-connected appliances 1512 (hereinafter referred to as "smart appliances 1512"), such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth. According to embodiments, the network-connected appliances 1512 are made compatible with the smart-home environment by cooperating with the respective manufacturers of the appliances. For example, the appliances can be space heaters, window AC units, motorized duct vents, etc. When plugged in, an appliance can announce itself to the smart-home network, such as by indicating what type of appliance it is, and it can automatically integrate with the controls of the smart-home. Such communication by the appliance to the smart home can be facilitated by any wired or wireless communication protocols known by those having ordinary skill in the art. The smart home also can include a variety of non-communicating legacy appliances 1540, such as old conventional washer/dryers, refrigerators, and the like which can be controlled, albeit coarsely (ON/OFF), by virtue of the smart wall plugs 1510. The smart-home environment 1500 can further include a variety of partially communicating legacy appliances 1542, such as infrared ("IR") controlled wall air conditioners or other IR-controlled devices, which can be controlled by IR signals provided by the hazard detectors 1504 or the smart wall switches 1508.

According to embodiments, the smart thermostats 1502, the hazard detectors 1504, the smart doorbells 1506, the smart wall switches 1508, the smart wall plugs 1510, and other devices of the smart-home environment 1500 are modular and can be incorporated into older and new houses. For example, the devices are designed around a modular platform consisting of two basic components: a head unit and a back plate, which is also referred to as a docking station. Multiple configurations of the docking station are provided so as to be compatible with any home, such as older and newer homes. However, all of the docking stations include a standard head-connection arrangement, such that any head unit can be removably attached to any docking station. Thus, in some embodiments, the docking stations are interfaces that serve as physical connections to the structure and the voltage wiring of the homes, and the interchangeable head units contain all of the sensors, processors, user interfaces, the batteries, and other functional components of the devices.

The smart-home environment 1500 may also include communication with devices outside of the physical home but within a proximate geographical range of the home. For example, the smart-home environment 1500 may include a pool heater monitor 1514 that communicates a current pool temperature to other devices within the smart-home environment 1500 or receives commands for controlling the pool temperature. Similarly, the smart-home environment 1500 may include an irrigation monitor 1516 that communicates information regarding irrigation systems within the smart-home environment 1500 and/or receives control information for controlling such irrigation systems. According to embodiments, an algorithm is provided for considering the geographic location of the smart-home environment 1500, such as based on the zip code or geographic coordinates of the home. The geographic information is then used to obtain data helpful for determining optimal times for watering; such data may include sun location information, temperature, due point, soil type of the land on which the home is located, etc.

By virtue of network connectivity, one or more of the smart-home devices of FIG. 15 can further allow a user to interact with the device even if the user is not proximate to the device. For example, a user can communicate with a device using a computer (e.g., a desktop computer, laptop computer, or tablet) or other portable electronic device (e.g., a smartphone) 1566. A webpage or app can be configured to receive communications from the user and control the device based on the communications and/or to present information about the device's operation to the user. For example, the user can view a current setpoint temperature for a device and adjust it, using a computer. The user can be in the structure during this remote communication or outside the structure.

As discussed, users can control and interact with the smart thermostat, hazard detectors 1504, and other smart devices in the smart-home environment 1500 using a network-connected computer or portable electronic device 1566. In some examples, some or all of the occupants (e.g., individuals who live in the home) can register their electronic device 1566 with the smart-home environment 1500. Such registration can be made at a central server to authenticate the occupant and/or the device as being associated with the home and to give permission to the occupant to use the device to control the smart devices in the home. An occupant can use their registered electronic device 1566 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that, instead of or in addition to registering electronic devices 1566, the smart-home environment 1500 makes inferences about which individuals live in the home and are therefore occupants and which electronic devices 1566 are associated with those individuals. As such, the smart-home environment "learns" who is an occupant and permits the electronic devices 1566 associated with those individuals to control the smart devices of the home.

In some embodiments, in addition to containing processing and sensing capabilities, each of the devices 1502, 1504, 1506, 1508, 1510, 1512, 1514, and 1516 (collectively referred to as "the smart devices") is capable of data communications and information sharing with any other of the smart devices, as well as to any central server or cloud-computing system or any other device that is network-connected anywhere in the world. The required data communications can be carried out using one or more of a variety of custom or standard wireless protocols (e.g., cellular, 3G/4G, Wi-Fi, ZigBee, 6LoWPAN, BLE, etc.) and/or any of a variety of custom or standard wired protocols (CAT6 Ethernet, HomePlug, etc.). One particularly useful protocol that can be used is the Thread protocol, which is promulgated by the Thread Group and based on 802.15.4, IETF IPv6, and 6LoWPAN. For some embodiments, devices that are powered by the household mains current, either directly or through an AC power adapter, can be provided with a combination of Wi-Fi, which can be relatively power-intensive, along with one or more lower-power protocols such as Thread and/or BLE. In contrast, devices that are power-constrained in that they are not powered by the household mains current and do not have access to a high-capacity battery source are provided only with one or more low-power protocols such as Thread and/or BLE. In some cases, devices that are not powered by the household mains current, but do have access to a reasonably high-capacity battery source, can be provided with a combination of Wi-Fi and one or more lower-power protocols such as Thread and/or BLE, with the Wi-Fi communications being controlled to be temporally restricted, such as being turned on only during brief periodic time intervals (e.g., once per day to upload logs and receive updates from the cloud), during particular device-sensed events, or when the user has physically actuated the device such as by pressing a button on the device. The hazard detectors described herein can be provided in two different SKUs, one SKU being mains-powered with battery backup and the other SKU being battery only, albeit with a relatively large battery source (e.g., six lithium AA cells). For this battery-only SKU, the hazard detector is preferably provided with a combination of the temporally restricted Wi-Fi and one or more lower-power protocols such as Thread and/or BLE.

According to embodiments, all or some of the smart devices can serve as wireless or wired repeaters. For example, a first one of the smart devices can communicate with a second one of the smart devices via a wireless router 1560. The smart devices can further communicate with each other via a connection to a network, such as the Internet 1599. Through the Internet 1599, the smart devices can communicate with a cloud-computing system 1564, which can include one or more centralized or distributed server systems. The cloud-computing system 1564 can be associated with a manufacturer, support entity, or service provider associated with the device. For one embodiment, a user may be able to contact customer support using a device itself rather than needing to use other communication means such as a telephone or Internet-connected computer. Further, software updates can be automatically sent from cloud-computing system 1564 to devices (e.g., when available, when purchased, or at routine intervals).

According to embodiments, the smart devices combine to create a mesh network of spokesman and low-power nodes in the smart-home environment 1500, where some of the smart devices are "spokesman" nodes and others are "low-powered" nodes. Some of the smart devices in the smart-home environment 1500 are battery powered, while others have a regular and reliable power source, such as by connecting to wiring (e.g., to 120V line voltage wires) behind the walls 1554 of the smart-home environment. The smart devices that have a regular and reliable power source are referred to as "spokesman" nodes. These nodes are equipped with the capability of using any wireless protocol or manner to facilitate bidirectional communication with any of a variety of other devices in the smart-home environment 1500 as well as with the cloud-computing system 1564. On the other hand, the devices that are battery powered are referred to as "low-power" nodes. These nodes tend to be smaller than spokesman nodes and can only communicate using wireless protocols that require very little power, such as Zigbee, 6LoWPAN, etc. Further, some, but not all, low-power nodes are incapable of bidirectional communication. These low-power nodes send messages, but they are unable to "listen". Thus, other devices in the smart-home environment 1500, such as the spokesman nodes, cannot send information to these low-power nodes.

As described, the smart devices serve as low-power and spokesman nodes to create a mesh network in the smart-home environment 1500. Individual low-power nodes in the smart-home environment regularly send out messages regarding what they are sensing, and the other low-powered nodes in the smart-home environment—in addition to sending out their own messages—repeat the messages, thereby causing the messages to travel from node to node (i.e., device to device) throughout the smart-home environment 1500. The spokesman nodes in the smart-home environment 1500 are able to "drop down" to low-powered communication protocols to receive these messages, translate the messages to other communication protocols, and send the translated messages to other spokesman nodes and/or cloud-computing system 1564. Thus, the low-powered nodes using low-power communication protocols are able to send messages across the entire smart-home environment 1500 as well as over the Internet 1563 to cloud-computing system 1564. According to embodiments, the mesh network enables cloud-computing system 1564 to regularly receive data from all of the smart devices in the home, make inferences based on the data, and send commands back to one of the smart devices to accomplish some of the smart-home objectives described herein.

As described, the spokesman nodes and some of the low-powered nodes are capable of "listening." Accordingly, users, other devices, and cloud-computing system 1564 can communicate controls to the low-powered nodes. For example, a user can use the portable electronic device (e.g., a smartphone) 1566 to send commands over the Internet to cloud-computing system 1564, which then relays the commands to the spokesman nodes in the smart-home environment 1500. The spokesman nodes drop down to a low-power protocol to communicate the commands to the low-power nodes throughout the smart-home environment, as well as to other spokesman nodes that did not receive the commands directly from the cloud-computing system 1564.

An example of a low-power node is a smart nightlight 1570. In addition to housing a light source, the smart nightlight 1570 houses an occupancy sensor, such as an ultrasonic or passive IR sensor, and an ambient light sensor, such as a photoresistor or a single-pixel sensor that measures light in the room. In some embodiments, the smart nightlight 1570 is configured to activate the light source when its ambient light sensor detects that the room is dark and when its occupancy sensor detects that someone is in the room. In other embodiments, the smart nightlight 1570 is simply configured to activate the light source when its ambient light sensor detects that the room is dark. Further, according to embodiments, the smart nightlight 1570 includes a low-power wireless communication chip (e.g., ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly, using the mesh network, from node to node (i.e., smart device to smart device) within the smart-home environment 1500 as well as over the Internet 1599 to cloud-computing system 1564.

Other examples of low-powered nodes include battery-operated versions of the hazard detectors 1504. These hazard detectors 1504 are often located in an area without access to constant and reliable (e.g., structural) power and, as discussed in detail below, may include any number and type of sensors, such as smoke/fire/heat sensors, carbon monoxide/dioxide sensors, occupancy/motion sensors, ambient light sensors, temperature sensors, humidity sensors, and the like. Furthermore, hazard detectors 1504 can send messages that correspond to each of the respective sensors to the other devices and cloud-computing system 1564, such as by using the mesh network as described above.

Examples of spokesman nodes include smart doorbells 1506, smart thermostats 1502, smart wall switches 1508, and smart wall plugs 1510. These devices 1502, 1506, 1508, and 1510 are often located near and connected to a reliable power source, and therefore can include more power-consuming components, such as one or more communication chips capable of bidirectional communication in any variety of protocols.

In some embodiments, the mesh network of low-powered and spokesman nodes can be used to provide exit lighting in the event of an emergency. In some instances, to facilitate this, users provide pre-configuration information that indicates exit routes in the smart-home environment 1500. For example, for each room in the house, the user provides a map of the best exit route. It should be appreciated that instead of a user providing this information, cloud-computing system 1564 or some other device could automatically determine the routes using uploaded maps, diagrams, architectural drawings of the smart-home house, as well as using a map generated based on positional information obtained from the nodes of the mesh network (e.g., positional information from the devices is used to construct a map of the house). In operation, when an alarm is activated (e.g., when one or more of the hazard detector 1504 detects smoke and activates an alarm), cloud-computing system 1564 or some other device uses occupancy information obtained from the low-powered and spokesman nodes to determine which rooms are occupied and then turns on lights (e.g., smart nightlights 1570, wall switches 1508, smart wall plugs 1510 that power lamps, etc.) along the exit routes from the occupied rooms so as to provide emergency exit lighting.

Further included and illustrated in the exemplary smart-home environment 1500 of FIG. 15 are service robots 1562 each configured to carry out, in an autonomous manner, any of a variety of household tasks. For some embodiments, the service robots 1562 can be respectively configured to perform floor sweeping, floor washing, etc. in a manner similar to that of known commercially available devices such as the Roomba™ and Scooba™ products sold by iRobot, Inc. of Bedford, Mass. Tasks such as floor sweeping and floor washing can be considered as "away" or "while-away" tasks for purposes of the instant description, as it is generally more desirable for these tasks to be performed when the occupants are not present. For other embodiments, one or more of the service robots 1562 are configured to perform tasks such as playing music for an occupant, serving as a localized thermostat for an occupant, serving as a localized air monitor/purifier for an occupant, serving as a localized baby monitor, serving as a localized hazard detector for an occupant, and so forth, it being generally more desirable for such tasks to be carried out in the immediate presence of the human occupant. For purposes of the instant description, such tasks can be considered as "human-facing" or "human-centric" tasks.

When serving as a localized air monitor/purifier for an occupant, a particular service robot 1562 can be considered to be facilitating what can be called a "personal health-area network" for the occupant, with the objective being to keep the air quality in the occupant's immediate space at healthy levels. Alternatively or in conjunction therewith, other health-related functions can be provided, such as monitoring the temperature or heart rate of the occupant (e.g., using finely remote sensors, near-field communication with on-person monitors, etc.). When serving as a localized hazard detector for an occupant, a particular service robot 1562 can be considered to be facilitating what can be called a "personal safety-area network" for the occupant, with the objective being to ensure there is no excessive carbon monoxide, smoke, fire, etc., in the immediate space of the occupant. Methods analogous to those described above for personal comfort-area networks in terms of occupant identifying and tracking are likewise applicable for personal health-area network and personal safety-area network embodiments.

According to some embodiments, the above-referenced facilitation of personal comfort-area networks, personal health-area networks, personal safety-area networks, and/or other such human-facing functionalities of the service robots 1562, are further enhanced by logical integration with other smart sensors in the home according to rules-based inferencing techniques or artificial intelligence techniques for achieving better performance of those human-facing functionalities and/or for achieving those goals in energy-conserving or other resource-conserving ways. Thus, for one embodiment relating to personal health-area networks, the air monitor/purifier service robot 1562 can be configured to detect whether a household pet is moving toward the currently settled location of the occupant (e.g., using on-board sensors and/or by data communications with other smart-home sensors along with rules-based inferencing/artificial intelligence techniques), and if so, the air purifying rate is immediately increased in preparation for the arrival of more airborne pet dander. For another embodiment relating to personal safety-area networks, the hazard detector service robot 1562 can be advised by other smart-home sensors that the temperature and humidity levels are rising in the kitchen, which is nearby the occupant's current dining room location, and responsive to this advisory, the hazard detector service robot 1562 will temporarily raise a hazard detection threshold, such as a smoke detection threshold, under an inference that any small increases in ambient smoke levels will most likely be due to cooking activity and not due to a genuinely hazardous condition.

According to one embodiment, the user can be provided with a suite of related smart-home devices, such as may be provided by a common manufacturer or group or badged to work with a common "ecosystem" of that manufacturer or group, wherein each of the devices, where practicable, provides a same or similarly triggered illumination-based notification scheme and theme, such that the user can be readily familiar with the status signals emitted by the variety of different devices without needing to learn a different scheme for each device. Thus, by way of example, there can be provided a suite of devices including a security/automation hub, multiple door/window sensors, and multiple hazard detectors, wherein each such device has a circular illumination ring that conveys triggered visual information according to the themes and schemes described herein.

Figure 16A:
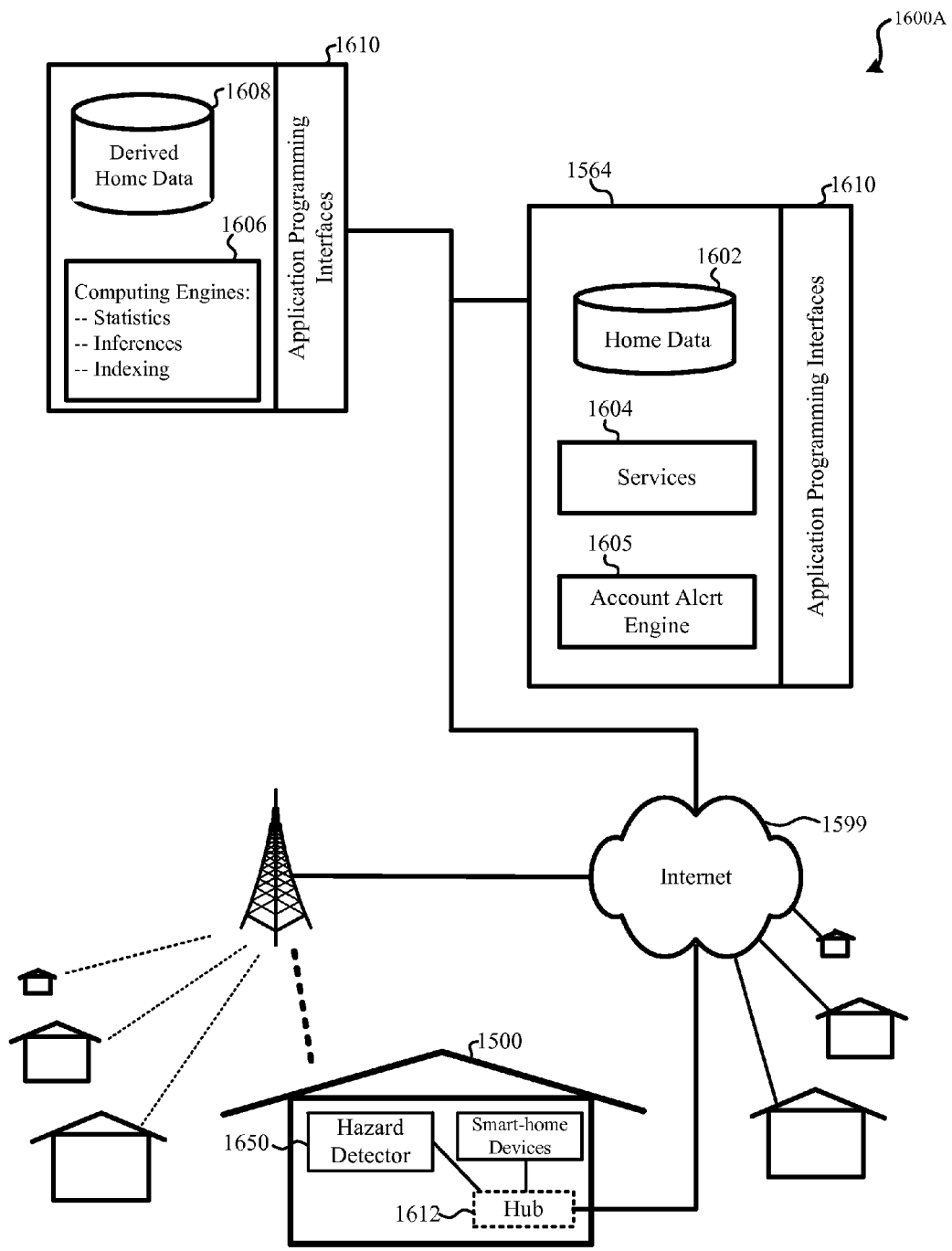
FIG. 16A illustrates a network-level view of the extensible devices and services platform with which a hazard detector may be integrated.

FIG. 16A illustrates a network-level view of an extensible devices and services platform 1600A with which a plurality of smart-home environments, such as the smart-home environment 1500 of FIG. 15, can be integrated. The extensible devices and services platform 1600A includes cloud-computing system 1564. Each of the intelligent, network-connected devices 1502, 1504, 1506, 1508, 1510, 1512, 1514, and 1516 from FIG. 15 may communicate with cloud-computing system 1564. For example, a connection to the Internet 1599 can be established either directly (for example, using 3G/4G connectivity to a wireless carrier), through a hubbed network 1612 (which can be a scheme ranging from a simple wireless router, for example, up to and including an intelligent, dedicated whole-home control node), or through any combination thereof.

Although in some examples provided herein, the devices and services platform 1600A communicates with and collects data from the smart devices of smart-home environment 1500 of FIG. 15, it should be appreciated that the devices and services platform 1600A communicates with and collects data from a plurality of smart-home environments across the world. For example, cloud-computing system 1564 can collect home data 1602 from the devices of one or more smart-home environments, where the devices can routinely transmit home data or can transmit home data in specific instances (e.g., when a device queries the home data 1602). Thus, the devices and services platform 1600A routinely collects data from homes across the world. As described, the collected home data 1602 includes, for example, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

Cloud-computing system 1564 can further provide one or more services 1604. The services 1604 can include, e.g., software updates, customer support, sensor data collection/logging, remote access, remote or distributed control, or use suggestions (e.g., based on collected home data 1602 to improve performance, reduce utility cost, etc.). Data associated with the services 1604 can be stored at cloud-computing system 1564 and cloud-computing system 1564 can retrieve and transmit the data at an appropriate time (e.g., at regular intervals, upon receiving a request from a user, etc.).

As part of services 1604, user accounts may be maintained by the cloud-computing system 1564. The user account may store subscription information, billing information, registration information, user preferences, and/or other data associated with various smart-home devices, such as one or more hazard detectors, installed within a structure that is linked with a user account. Occasionally, attention of a user to his or her user account may be requested. In response to a query from hazard detector 1650 (or other smart-home device), a message may be transmitted by the cloud-computing system 1564 to hazard detector 1650 (which may represent any of the previously described hazard detectors) indicating that a status output by hazard detector 1650 should indicate that a user is requested to log in to his or her user account. Further detail regarding the requested log may be transmitted by service 1604 to hazard detector 1650. For instance, the reason for the requested login may be expired payment information (such as an expired credit card). The user can request detail on a status output by hazard detector 1650, which may be presented to the user as a color and animation output via a light of hazard detector 1650. The request for detail may be by performing a gesture within the vicinity of hazard detector 1650. A spoken message may then be output by hazard detector 1650 indicating that the user is requested to log in to his account and may also indicate the reason of the payment information needing to be updated. As such, a status check performed by hazard detector 1650 may not only check the status of hazard detector 1650 itself, but also the state of a remotely-maintained user account.

As illustrated in FIG. 16, an embodiment of the extensible devices and services platform 1600A includes a processing engine 1606, which can be concentrated at a single server or distributed among several different computing entities without limitation. The processing engine 1606 can include computerized engines (e.g., software executed by hardware) configured to receive data from devices of smart-home environments (e.g., via the Internet 1599 or a hubbed network), to index the data, to analyze the data and/or to generate statistics based on the analysis or as part of the analysis. The analyzed data can be stored as derived home data 1608.

Results of the analysis or statistics can thereafter be transmitted back to the device that provided home data used to derive the results, to other devices, to a server providing a webpage to a user of the device, or to other non-device entities. For example, use statistics, use statistics relative to use of other devices, use patterns, and/or statistics summarizing sensor readings can be generated by the processing engine 1606 and transmitted. The results or statistics can be provided via the Internet 1599. In this manner, the processing engine 1606 can be configured and programmed to derive a variety of useful information from the home data 1602. A single server can include one or more engines.

In some embodiments, to encourage innovation and research and to increase products and services available to users, the devices and services platform 1600A exposes a range of application programming interfaces (APIs) 1610 to third parties, such as charities, governmental entities (e.g., the Food and Drug Administration or the Environmental Protection Agency), academic institutions (e.g., university researchers), businesses (e.g., providing device warranties or service to related equipment, targeting advertisements based on home data), utility companies, and other third parties. The APIs 1610 may be coupled to and permit third-party systems to communicate with cloud-computing system 1564, including the services 1604, the processing engine 1606, the home data 1602, and the derived home data 1608. For example, the APIs 1610 allow applications executed by the third parties to initiate specific data processing tasks that are executed by cloud-computing system 1564, as well as to receive dynamic updates to the home data 1602 and the derived home data 1608.

Account alert engine may serve to determine whether a hazard detector should provide an indication that the user's account requires attention. For instance, account alert engine 1605 may periodically assess the state of a user's account, such as whether settings need updating, whether payment information is up-to-date, whether one or more messages are pending, whether payment is due, etc. If user attention is required, upon a request being received from a hazard detector and a look-up of the user's account being performed, account alert engine may respond with an indication that the user account requires attention. Additional detail may also be provided such that if the user performs a gesture or otherwise requests additional detail, such detail can be provided, such as via an auditory message. If user attention is not required, upon a request being received from a hazard detector and a look-up of the user's account being performed (e.g., by determining an account associated with the hazard detector from which the request was received), account alert engine may respond with an indication that the user account does not require attention.

Figure 16B:
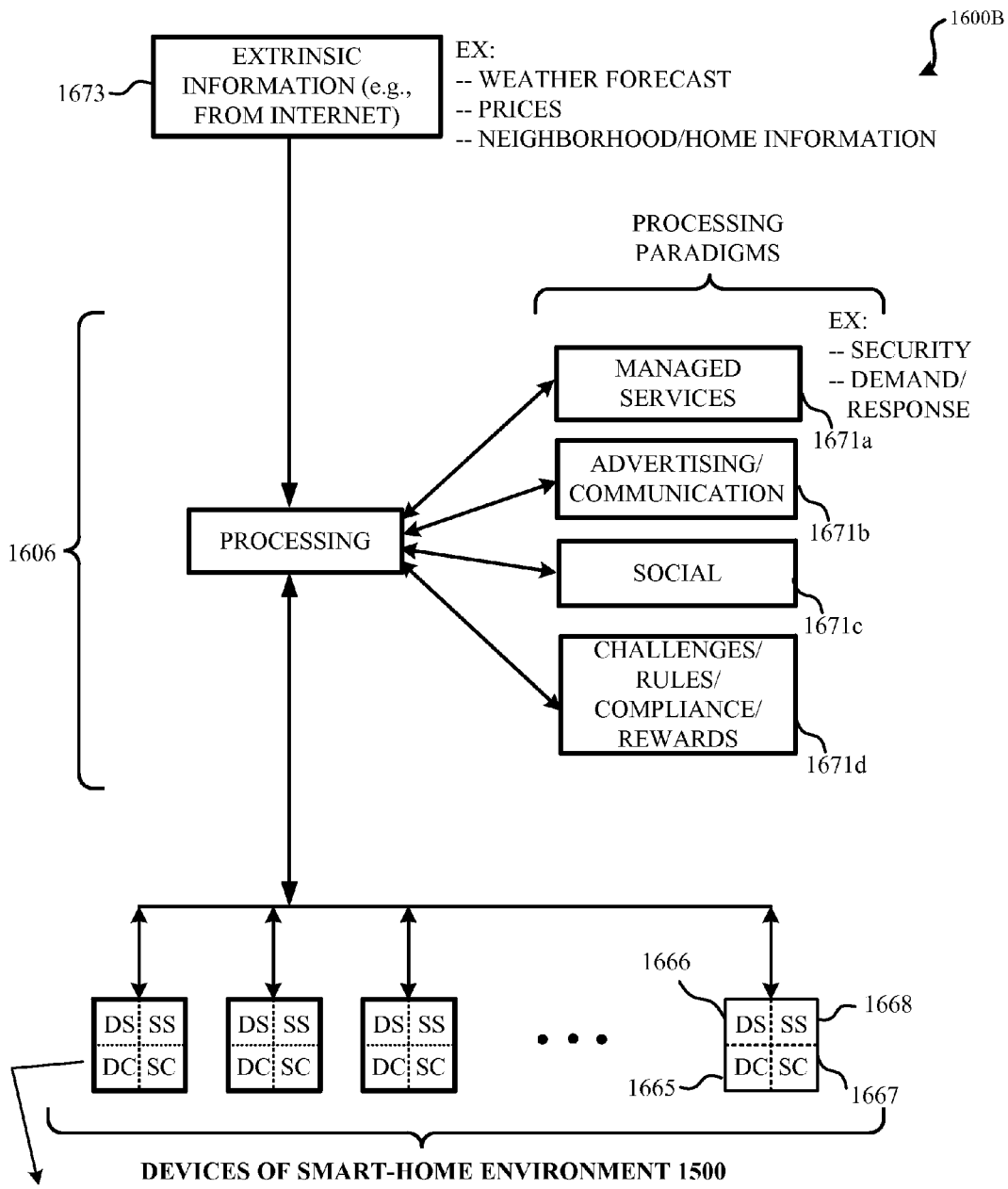
FIG. 16B illustrates an embodiment of an abstracted functional view of the extensible devices and services platform of FIG. 16A, with reference to a processing engine as well as devices of the smart-home environment.

FIG. 16B illustrates an abstracted functional view 1600B of the extensible devices and services platform 1600A of FIG. 16A, with particular reference to the processing engine 1606 as well as devices, such as those of the smart-home environment 1500 of FIG. 15. Even though devices situated in smart-home environments will have an endless variety of different individual capabilities and limitations, they can all be thought of as sharing common characteristics in that each of them is a data consumer 1665 (DC), a data source 1666 (DS), a services consumer 1667 (SC), and a services source 1668 (SS). Advantageously, in addition to providing the essential control information needed for the devices to achieve their local and immediate objectives, the extensible devices and services platform 1600A can also be configured to harness the large amount of data that is flowing out of these devices. In addition to enhancing or optimizing the actual operation of the devices themselves with respect to their immediate functions, the extensible devices and services platform 1600A can be directed to "repurposing" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

For example, FIG. 16B shows processing engine 1606 as including a number of paradigms 1671. Processing engine 1606 can include a managed services paradigm 1671a that monitors and manages primary or secondary device functions. The device functions can include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, or alerting a user of a current or predicted future event or characteristic. Processing engine 1606 can further include an advertising/communication paradigm 1671b that estimates characteristics (e.g., demographic information), desires and/or products of interest of a user based on device usage. Services, promotions, products or upgrades can then be offered or automatically provided to the user. Processing engine 1606 can further include a social paradigm 1671c that uses information from a social network, provides information to a social network (for example, based on device usage), and/or processes data associated with user and/or device interactions with the social network platform. For example, a user's status as reported to their trusted contacts on the social network could be updated to indicate when they are home based on light detection, security system inactivation or device usage detectors. As another example, a user may be able to share device-usage statistics with other users. In yet another example, a user may share HVAC settings that result in low power bills and other users may download the HVAC settings to their smart thermostat 1502 to reduce their power bills.

The processing engine 1606 can include a challenges/rules/compliance/rewards paradigm 1671d that informs a user of challenges, competitions, rules, compliance regulations and/or rewards and/or that uses operation data to determine whether a challenge has been met, a rule or regulation has been complied with and/or a reward has been earned. The challenges, rules or regulations can relate to efforts to conserve energy, to live safely (e.g., reducing exposure to toxins or carcinogens), to conserve money and/or equipment life, to improve health, etc. For example, one challenge may involve participants turning down their thermostat by one degree for one week. Those that successfully complete the challenge are rewarded, such as by coupons, virtual currency, status, etc. Regarding compliance, an example involves a rental-property owner making a rule that no renters are permitted to access certain owner's rooms. The devices in the room having occupancy sensors could send updates to the owner when the room is accessed.

The processing engine 1606 can integrate or otherwise utilize extrinsic information 1673 from extrinsic sources to improve the functioning of one or more processing paradigms. Extrinsic information 1673 can be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, etc., to identify statistical or environmental conditions, trends or other information associated with a home or neighborhood, and so forth.

An extraordinary range and variety of benefits can be brought about by, and fit within the scope of, the described extensible devices and services platform 1600A, ranging from the ordinary to the profound. Thus, in one "ordinary" example, each bedroom of the smart-home environment 1500 can be provided with a smart wall switch 1508, a smart wall plug 1510, and/or smart hazard detectors 1504, all or some of which include an occupancy sensor, wherein the occupancy sensor is also capable of inferring (e.g., by virtue of motion detection, facial recognition, audible sound patterns, etc.) whether the occupant is asleep or awake. If a serious fire event is sensed, the remote security/monitoring service or fire department is advised of how many occupants there are in each bedroom, and whether those occupants are still asleep (or immobile) or whether they have properly evacuated the bedroom. While this is, of course, a very advantageous capability accommodated by the described extensible devices and services platform, there can be substantially more "profound" examples that can truly illustrate the potential of a larger "intelligence" that can be made available. By way of perhaps a more "profound" example, the same bedroom occupancy data that is being used for fire safety can also be "repurposed" by the processing engine 1606 in the context of a social paradigm of neighborhood child development and education. Thus, for example, the same bedroom occupancy and motion data discussed in the "ordinary" example can be collected and made available (properly anonymized) for processing in which the sleep patterns of schoolchildren in a particular ZIP code can be identified and tracked. Localized variations in the sleeping patterns of the schoolchildren may be identified and correlated, for example, to different nutrition programs in local schools.

Figure 17:
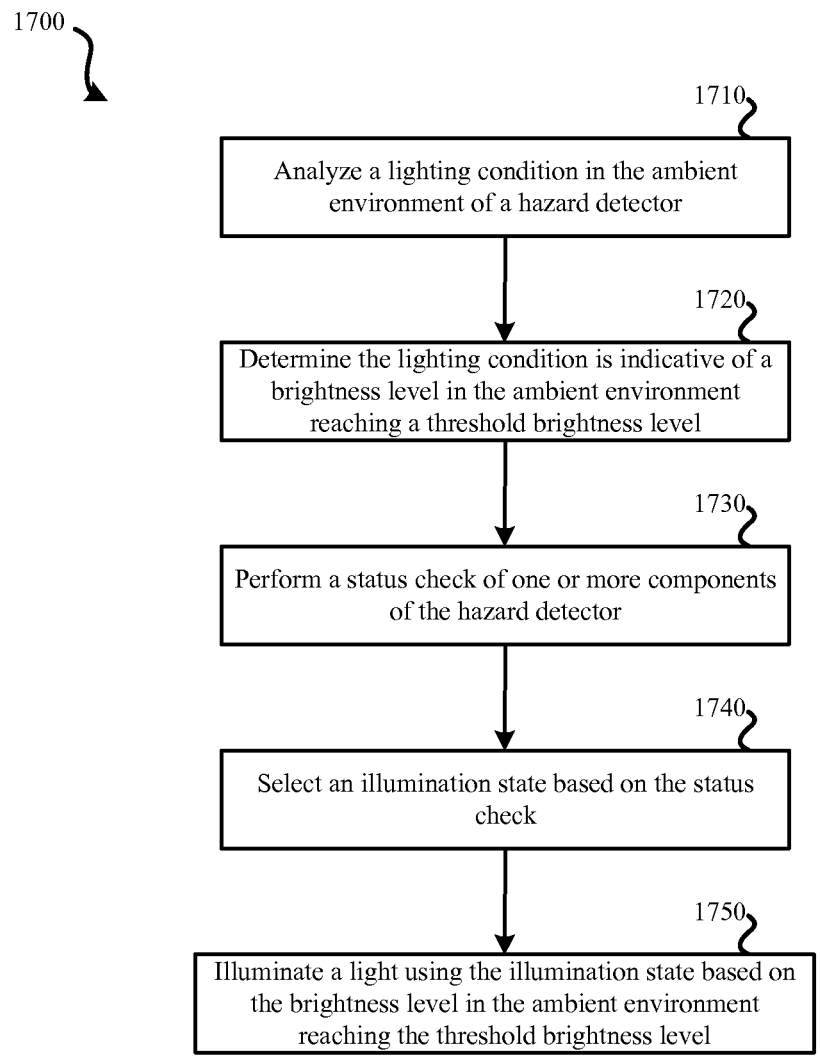
FIG. 17 illustrates an embodiment of a method for outputting a status of a hazard detector.

Various methods may be performed using the systems, devices, and other embodiments detailed in relation to FIGS. 1 through 16. For instance, methods may be performed by the hazard detectors detailed in relation to FIGS. 1 through 6. FIG. 17 illustrates an embodiment of a method 1700 for outputting a status of a hazard detector. Method 1700 represents various blocks which may be performed by a hazard detector, such as the hazard detector and/or other devices detailed in relation to FIGS. 1 through 6.

At block 1710, a lighting condition in the ambient environment of a hazard detector may be analyzed. Such analysis may include the collection of one or more measurements of a brightness level in the ambient environment of the hazard detector. A hazard detector may have one or more onboard light sensors that detect a level of brightness in the ambient environment of the hazard detector. The lighting condition in the ambient environment of the hazard detector may be affected by artificial lighting and/or natural lighting. An indication of the lighting condition may be provided by the one or more light sensors of the hazard detector to a processing system, which may include one or more processors, of the hazard detector. In some embodiments, the lighting condition in the ambient environment of the hazard detector may be analyzed directly by the lighting sensor, such as via an integrated processor. Means for performing block 1710 may generally include a hazard detector. More specifically, means for performing block 1710 may include one or more processing devices, such as processors, and one or more light sensors.

At block 1720, the lighting condition analyzed at block 1710 may be compared with a threshold brightness level value stored by the hazard detector. This comparison may be used to determine that the lighting condition is indicative of a brightness level in the ambient environment that has reached the threshold brightness level. In some embodiments, the determination of block 1720 may involve determining that the brightness level in the ambient environment of the hazard detector has decreased to, or fallen below, the threshold brightness level. As such, in some embodiments, block 1720 can be understood as determining that a falling edge of brightness within the ambient environment of the hazard detector has met the threshold brightness level. Means for performing block 1720 may generally include a hazard detector. More specifically, means for performing block 1720 may include one or more processing devices, such as processors, and a storage medium, such as to store the threshold brightness level.

At block 1730, a status check of one or more components of the hazard detector may be performed. In some embodiments, the status check performed as part of block 1730 is performed in response to block 1720; that is, the status check can be performed in response to determining that the lighting condition is indicative of the brightness level in the ambient environment of the hazard detector falling to the threshold brightness level. In other embodiments, the status check is performed independent of block 1720; that is, the status check is not dependent on determining that the lighting condition in the ambient environment of the hazard detector has reached the threshold brightness level. The status check performed at block 1730 may involving checking a status one or more components of the hazard detector. For instance, the status check may check a battery charge level of the hazard detector. The battery charge level may be compared to multiple threshold voltage levels. Such multiple levels may be used to assess whether: the battery has a sufficient charge level, the battery charge level is low (but does not need replacement yet), or the battery needs replacement immediately. The status check may check the functionality of one or more sensors of the hazard detector, such as a smoke sensor and/or a carbon monoxide sensor. In some embodiments, the status check involves checking an expiration date of one or more sensors of the hazard detector and/or of the hazard detector itself. For instance, smoke detectors and/or carbon monoxide detectors may be required by law to expire after a predefined amount of time, such as seven years. The status check of block 1730 may involve determining whether a structure power source, if installed and connected, is providing power. The status check of block 1730 may involve checking the status of a user account maintained remotely from the hazard detector. This may involve transmitting a request to a remote server, such as detailed in relation to FIGS. 15, 16A, and 16B, to determine the status of the user account. If the user account requires attention, the hazard detector may receive a message indicating as such, possibly with one or more details about the nature of the status, in response to the transmitted request. The status check performed at block 1730 may check whether a test of the hazard detector has been performed within a predefined amount of time. For instance, it may be desirable to provide a user with a warning if it has been more than some amount of time, such as a week a month, since a user last performed a test of the hazard detector (e.g., test that the audible alarms sound). A test may be different from status check in that a test may audibly sound one or more alarms of the hazard detector and/or may test the functionality of one or more sensors present on the hazard detector. Means for performing block 1730 may generally include a hazard detector. More specifically, means for performing block 1720 may include one or more processing devices, such as processors, and one or more components to be tested, such as one or more instances of the various components detailed in relation to hazard detector 200. Means for performing block 1730 may further include a remote server and one or more networks to communicate with the remote server.

At block 1740, an illumination state that is based on the status check may be selected. The illumination state may include one or more colors, an animation, and/or speed to illuminate a light of the hazard detector. As previously detailed, the light may include one or more lighting elements, such as LEDs. Such an arrangement may permit animations and multiple colors to be presented by the light simultaneously. A lookup table or other storage arrangement of definitions of illumination states associated with results of status checks may be stored by the hazard detector. For example, lookup tables corresponding to FIGS. 12 and 13 may be used to determine the appropriate illumination state to be presented by the hazard detector in response to a status check. Similarly, information presented in such lookup tables may be provided to users, such as in the form of the user manual or quick reference guide such to allow the user to interpret the various illumination states. The result of the status check performed at block 1730 may be used to determine the proper illumination state to be selected at block 1740. Means for performing block 1740 may generally include a hazard detector. More specifically, means for performing block 1740 may include one or more processing devices, such as processors, and a storage medium, such as to store the definitions of various illumination states.

At block 1750, the light of the hazard detector may be illuminated based on the illumination state selected at block 1740. In some embodiments, the performance of block 1750 is contingent on block 1720. That is, while the status check performed at block 1730 may not be contingent on determining that the lighting condition in the ambient environment of the hazard detector has reached the threshold brightness level, illumination of the light using the illumination state indicative of the results of the status check may be based on the lighting condition in the ambient environment of the hazard detector reaching the threshold brightness level. Stated another way, the brightness level in the ambient environment of the hazard detector may be used to determine when to present the results of the status check but not when to perform the status check. In other embodiments, such as embodiments in which the status check of block 1730 is performed in response to block 1720, the illumination of block 1750 may occur in response to blocks 1730 and 1740 being performed.

The illumination of block 1750 may occur for a predefined period of time. For example, the light may be illuminated for periods of time ranging from 1 to 5 seconds, or some other period of time. In some embodiments, the light fades on for one second, presents an illumination state for one second, then fades off for one second. It should be understood that by waiting for the lighting condition in the ambient environment of the hazard detector to decrease to the threshold brightness level, a user may be more likely to view the illumination state at block 1750 because the ambient environment of the hazard detector is darkened (as compared to a previous lighting condition of the ambient environment). As an example, a likely situation where a user may view the illuminated light at block 1750 is when shutting off an artificial light source in a room in which the hazard detector is located. The light may be more likely to illuminate at night if natural light enters the room by day. Therefore, the user may typically view the illumination indicative of the status test in the evening when shutting off an artificial light. Means for performing block 1750 may generally include a hazard detector. More specifically, means for performing block 1750 may include one or more processing devices, such as processors, and one or more lights, which may each include one or more lighting elements.

Figure 18:
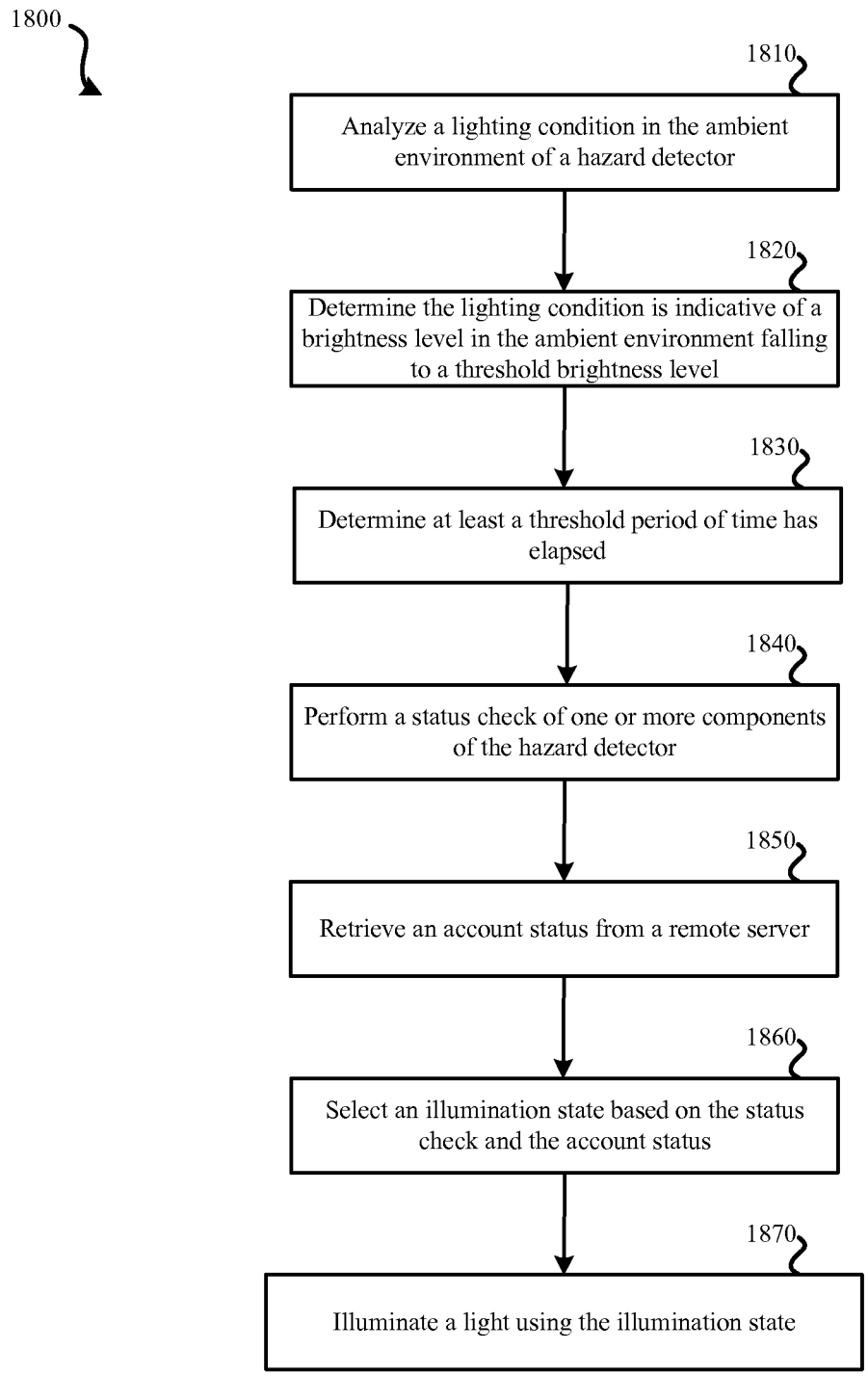
FIG. 18 illustrates another embodiment of a method for outputting a status of a hazard detector.

FIG. 18 illustrates an embodiment of a method 1800 for outputting a status of a hazard detector. Method 1800 may represent an alternate or more detailed embodiment of method 1700. Method 1800 represents various blocks which may be performed by a hazard detector, such as the hazard detector and/or other devices detailed in relation to FIGS. 1 through 6.

Blocks 1810 and 1820 may be performed similarly to blocks 1710 and 1720 of method 1700, respectively. Means for performing such blocks may generally include a hazard detector. More specifically, means for performing such blocks may include one or more processing devices, such as processors, one or more light sensors, and one or more storage mediums.

At block 1830, a determination may be made as to whether at least a threshold period of time has elapsed since: a previous status check, a previous illumination of a light of the hazard detector indicative of the status, and/or a previous determination that the lighting condition is indicative of a brightness level in the ambient environment of the hazard detector dropping below a threshold brightness level. Block 1830 may be used to ensure that status checks or the output of illumination states indicative of the result of status checks do not occur overly frequently. For example, it may be desired that the threshold period of time be one month, one week, one day, ten hours, five hours, an hour, ten minutes, one minute, or some other period of time between the listed periods of time. In a likely situation, it may be desirable for a status check to be performed and/or the result of the status check to presented once per day. Such a restriction may help preserve battery charge and/or prevent a user from being annoyed by overly frequently presented statuses. Means for performing block 1830 may generally include a hazard detector. More specifically, means for performing block 1830 may include one or more processing devices, such as a processor and one or more storage mediums.

At block 1840, the status check may be performed. The status check of block 1840 may be performed similarly to block 1730 of method 1700. If performance of the status check is contingent on the lighting condition indicative of the brightness level in the ambient environment falling to a threshold brightness level, the performance of the status check may be additionally contingent on block 1830 determining that at least the threshold period of time has elapsed since the previous status check. Means for performing block 1840 may generally include a hazard detector. More specifically, means for performing block 1840 may include one or more processing devices, such as processors, and one or more components to be tested, such as one or more instances of the various components detailed in relation to hazard detector 200 of FIG. 2.

At block 1850, the hazard detector may transmit a message to a remote server to check a status of an account held by a user, the hazard detector having previously been added to and linked with a user account. For instance, the user account may be used to manage multiple smart home devices, including the hazard detector, that are installed within a particular home or other form of structure. The message may be sent to the remote server roughly periodically (e.g., once per day, once per week), or may occur in response to a condition occurring, such as block 1840 being performed, block 1830 being performed, and/or block 1820 being performed. In response to the message, the remote server (which may be part of cloud-computing system 1564 of FIG. 15) may check the status of the user account associated with the hazard detector. Checking the status of the user account may include: checking if the last login by the user was within a predefined period of time, checking if any messages are pending for viewing by the user, checking if the user's payment information is valid, checking if any offers are waiting for review by the user, checking if any settings or preferences require the user's attention, checking if a new end-user agreement (or other document) needs to be reviewed by the user, and/or checking if any other form of matter requires the user's attention. In some embodiments, the remote server may occasionally push a status of the user's account to the hazard detector without receiving a request from the hazard detector. Means for performing block 1850 may generally include a hazard detector. More specifically, means for performing block 1850 may include one or more processing devices, such as processors, a wireless communication module, one or more networks, and/or a remote server.

At block 1860, an illumination state may be selected based on the status check of block 1840 and the account status retrieved at block 1850. The illumination state may include one or more colors, an animation, and/or speed to illuminate a light of the hazard detector. As previously detailed, the light may include one or more lighting elements, such as LEDs. Such an arrangement may permit animations and multiple colors to be presented by the light simultaneously. A lookup table or other storage arrangement of definitions of illumination states associated with results of status checks may be stored by the hazard detector. For example, lookup tables corresponding to FIGS. 12 and 13 may be used to determine the appropriate illumination state to be presented by the hazard detector in response to a status check. Similarly, information presented in such lookup tables may be provided to user, such as in the form of the user manual or quick reference guide such to allow the user to interpret the illumination state. The result of the status check performed at block 1840 and the account status of block 1850 may be used to determine the proper illumination state to be selected at block 1860. Means for performing block 1860 may generally include a hazard detector. More specifically, means for performing block 1860 may include one or more processing devices, such as processors, and a storage medium, such as to store the definitions of various illumination states.

At block 1870, the light may be illuminated according to the illumination state selected at block 1860. In some embodiments, the performance of block 1870 is contingent on the determinations of blocks 1820 and 1830. That is, while the status check performed at block 1840 may not be contingent on determining that the lighting condition in the ambient environment of the hazard detector has reached the threshold brightness level (or that the predefined period of time has elapsed), illumination of the light using the illumination state indicative of the results of the status check (and/or account status) may be based on the lighting condition in the ambient environment of the hazard detector reaching the threshold brightness level and the threshold period of time having elapsed. Stated another way, the brightness level in the ambient environment of the hazard detector and the predefined period of time having elapsed may be used to determine when to present the results of the status check (which may include the account status check) but not when to perform the status check. In other embodiments, block 1870 may be performed in response to blocks 1840, 1850, and/or 1860 being completed. Means for performing block 1860 may generally include a hazard detector. More specifically, means for performing block 1860 may include one or more processing devices, such as processors, and one or more lights, which may each include one or more lighting elements.

Figure 19:
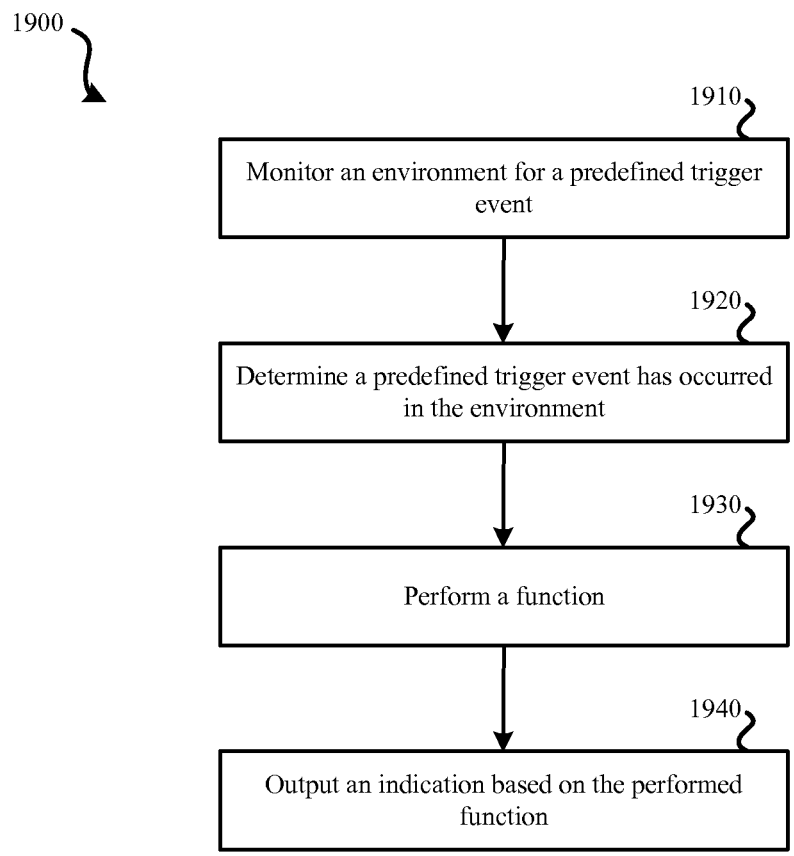
FIG. 19 illustrates an embodiment of a method for performing a function in response to an unrelated environmental characteristic.

While methods 1700 and 1800 of FIGS. 17 and 18, respectively, are focused on hazard detectors, such methods may be applied to devices and systems other than hazard detectors. FIG. 19 illustrates an embodiment of a method 1900 for performing a function in response to an unrelated environmental characteristic. Method 1900 represents various blocks which may be performed by a system or device, which may or may not be a hazard detector. For example, the device or system may be a device configured to sense or monitor a situation, such as temperature, humidity, motion, etc. Each block of method 1900 may be performed by such a device.

At block 1910, an environment may be monitored for the presence of a trigger event. The environment may be monitored in the vicinity of the device performing method 1900. For instance, the device may have one or more sensors installed that are configured to measure a characteristic present in the environment. This collected data may be monitored for the stored, predefined trigger event. Examples include: monitoring for a temperature, monitoring for a humidity, monitoring for a brightness, monitoring for motion, etc. In some embodiments, the trigger event may be received from a remote device or system, such as via a wireless network connection. Means for performing block 1910 may generally include a device or system such as in FIG. 3. More specifically, means for performing block 1910 may include one or more processing devices, such as processors, and an event detection module, which may include one or more types of sensors.

At block 1920, a predefined trigger event may be determined to have occurred in the environment. Monitoring the environment at block 1910 may have resulted in data being gathered that indicates the predefined trigger event, of which a definition is stored by the system, is determined to have occurred. Examples include: the monitored temperature having reached a threshold temperature, the monitored humidity having reached a humidity threshold, the monitored brightness having reached a brightness threshold, motion being determined to have occurred, etc. Means for performing block 1920 may generally include a device or system such as in FIG. 3. More specifically, means for performing block 1920 may include one or more processing devices, such as processors, an event detection module, which may include one or more types of sensors, and a processor-readable medium, to store a definition of the predefined trigger event.

At block 1930, a function may be performed. The function performed at block 1930 may be performed in response to the predefined trigger event determining to occurred. In other embodiments, the function performed at block 1930 may occur according to a predefined schedule or contingent on the occurrence of some event other than the trigger event of block 1920. Means for performing block 1930 may generally include a device or system such as in FIG. 3. More specifically, means for performing block 1930 may include one or more processing devices, such as processors, and a function component (which, in some embodiments, may be the one or more processing devices).

It should be understood that the function of block 1930 may be wholly unrelated to the trigger event of block 1920. For instance, the trigger event of block 1920 may be selected based on an event that will likely correspond to a time when a user desires to view a status of a function. For example, the function of block 1930 may be a self-test, status check of the device performing method 1900, or some other form of function. The predefined trigger event for which the environment is monitored at block 1910 and which is determined to have occurred at block 1920, may be wholly unrelated to this self-test and/or status check. As such, the trigger event may be selected based on its likely correlation to a time at which a user would desire information about the results of a function, regardless of whether the function is performed in response to the trigger event or not.

At block 1940, an indication may be output based on the performed function. Output at block 1940 may be contingent on the predefined trigger event having occurred as determined at block 1920. Accordingly, an output that is based on the performed function may be output in response to the predefined trigger event having occurred, which may be wholly unrelated to the function itself. An example of this may be seen in various embodiments of methods 1700 and 1800. In some embodiments, a status of a hazard detector is output in response to a lighting condition present in the environment of the hazard detector. Such a lighting condition may be wholly unrelated to the status of the hazard detector (that is, brightness may have no effect on the status). In other embodiments, such as embodiments in which the function of block 1930 is performed in response to block 1920, block 1940 may be performed in response to block 1930 having been performed. The indication output at block 1940 may be indicative of a result of the function of block 1930. The output of block 1940 may include light and/or sound. For example, the output may be a combination of a color of the light, animation, and/or speed. Sound output may include a ring, tone, or spoken message. Other forms of output are of course possible, such as vibration, a printed message, or a transmission of a wireless message. Means for performing block 1940 may generally include a device or system such as in FIG. 3. More specifically, means for performing block 1940 may include one or more processing devices, such as processors, and an output module (which, in some embodiments, may include a speaker and/or a light, which can have one or more lighting elements, a vibration device, a printer, etc.).

Figure 20:
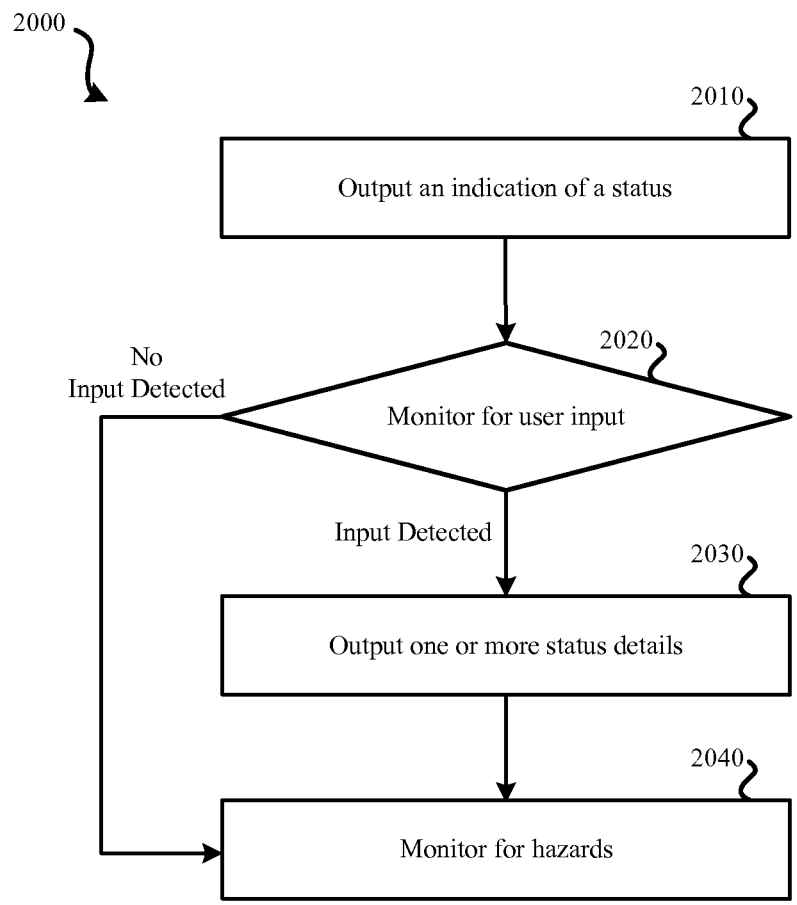
FIG. 20 illustrates an embodiment of a method for providing detail about a status in response to user input.

Following any of methods 1700 through 1900 being performed, it may be desirable to monitor for user input to determine if a user desires more information on a status (or other information) output by the hazard detector or other form of system or device. FIG. 20 illustrates an embodiment of method 2000 for providing detail about a status in response to user input. Method 2000 may be performed by a hazard detector following performing one of methods 1700 through 1900 or some other method for outputting a condition or status of the hazard detector. Each block of method 2000 may be performed by a hazard detector.

Block 2010 may represent the conclusion of methods 1700 through 1900. For instance block 2010 may represent block 1750 of method 1700, block 1870 of method 1800, and/or block 1940 of method 1900. Block 2010 may also represent some other indication of a status being output. For instance, in some embodiments, block 2010 may be performed without at least one of methods 1700 through 1900 being performed.

At block 2020, the hazard detector or other device may monitor for user input following the indication of the status being output at block 2010. In some embodiments, block 2020 may be triggered by some other condition occurring. For instance, the lighting condition reaching a brightness level in the ambient environment of the hazard detector that matches or is below the threshold brightness level may serve as a trigger for block 2020 or block 2010 may trigger block 2020. Monitoring for user input may include activating one or more sensors that are configured to monitor for user input. For example, a motion sensor or similar component may be activated for block 2020 to monitor for a gesture being performed by user. Such a gesture may be one or multiple waves by a user. Such a sensor may only be enabled to monitor for the gesture for up to a predefined period of time in order to conserve power, which may be especially useful in a battery-powered device. If the user input is detected, the sensor may be disabled because no immediate future user input needs to be monitored for. Means for performing block 2020 may generally include a hazard detector (or other form of device). More specifically, means for performing block 2020 may include one or more processing devices, such as processors, and one or more sensors, such as a motion sensor.

Method 2000 may proceed to block 2040 if no user input is received at block 2020. If user input is received at block 2020, method 2000 may proceed to block 2030. For instance, method 2000 may proceed to block 2030 if a user performs a wave gesture at block 2020 that is detected by the hazard detector. At block 2030, in response to user input being detected or otherwise received, one or more details regarding the status previously output at block 2010 may be provided; the one or more details provided at block 2030 may be provided via a different mode than the status of block 2010. For example, the status output at block 2010 may have been in the form of light, such as the previously described colors, animations, and/or speeds of lighting elements. The output of one or more status details of block 2030 may be via a different mode, such as an audio-based message. In some embodiments, the one or more status details of block 2030 are output in the form of the spoken message. This may involve the hazard detector retrieving, either from a local storage medium or from a remote server, a recorded message to be played via a speaker to the user. While the detail is being output, the status output at block 2020 may also be output, such that the status is in the form of light and the detail is in the form of audio. Means for performing block 2030 may generally include a hazard detector (or other form of device). More specifically, means for performing block 2030 may include one or more processing devices, such as processors, and one or more audio output devices, such as a speaker. It should be understood, that the one or more status details output at block 2030 may be output in some format other than audio. For instance, if the hazard detector has a screen, a written message or graphical indicator may be presented in addition to or alternatively to an auditory message.

As an example, at block 2010, a yellow illuminated status may be output to the user. The user may see the status in the form of a color and animation output by a light of a hazard detector and may understand that the hazard detector requires some form of attention; however the user may be unsure exactly what aspect of the hazard detector requires attention. If the user does not wish to deal with the situation presently, the user may simply not provide any input, such as a gesture. However, if the user is interested in learning one or more details as to what aspect of the hazard detector requires attention, the user may provide input, such as by pushing a button on the hazard detector or performing a gesture, such as one or more wave gestures during the predefined period of time for which the hazard detector is monitoring for user input. In response to the user providing the input, an auditory message containing one or more details about the status may be output by the hazard detector. For instance, the message may state: "My battery is low. Please replace at your earliest convenience." Following such a message being output, the user may understand the detailed aspect of the hazard detector that requires attention: the battery needs to be replaced. It should be understood that the same indication of the status may be output for various conditions of the hazard detector. In some embodiments, only by the user providing input in response to the status can the user learn precisely the aspect of the hazard detector that requires attention.

Regardless of whether user input was or was not received at block 2020, at block 2040, the hazard detector may continue to monitor for one or more hazards. Such hazards may include the monitoring for smoke and/or carbon monoxide. Further, monitoring for such hazards may occur throughout method 2000. Regardless of the portion of method 2000 being performed, a primary function of the hazard detector may be to continue to monitor for such hazards. As such, if a hazard is detected at any point during method 2000, method 2000 may be interrupted and an appropriate alarm may sound. Means for performing block 2040 may generally include a hazard detector (or other form of device). More specifically, means for performing block 2040 may include one or more processing devices, such as processors, and one or more sensors, such as smoke and/or carbon monoxide sensors.

Figure 21:
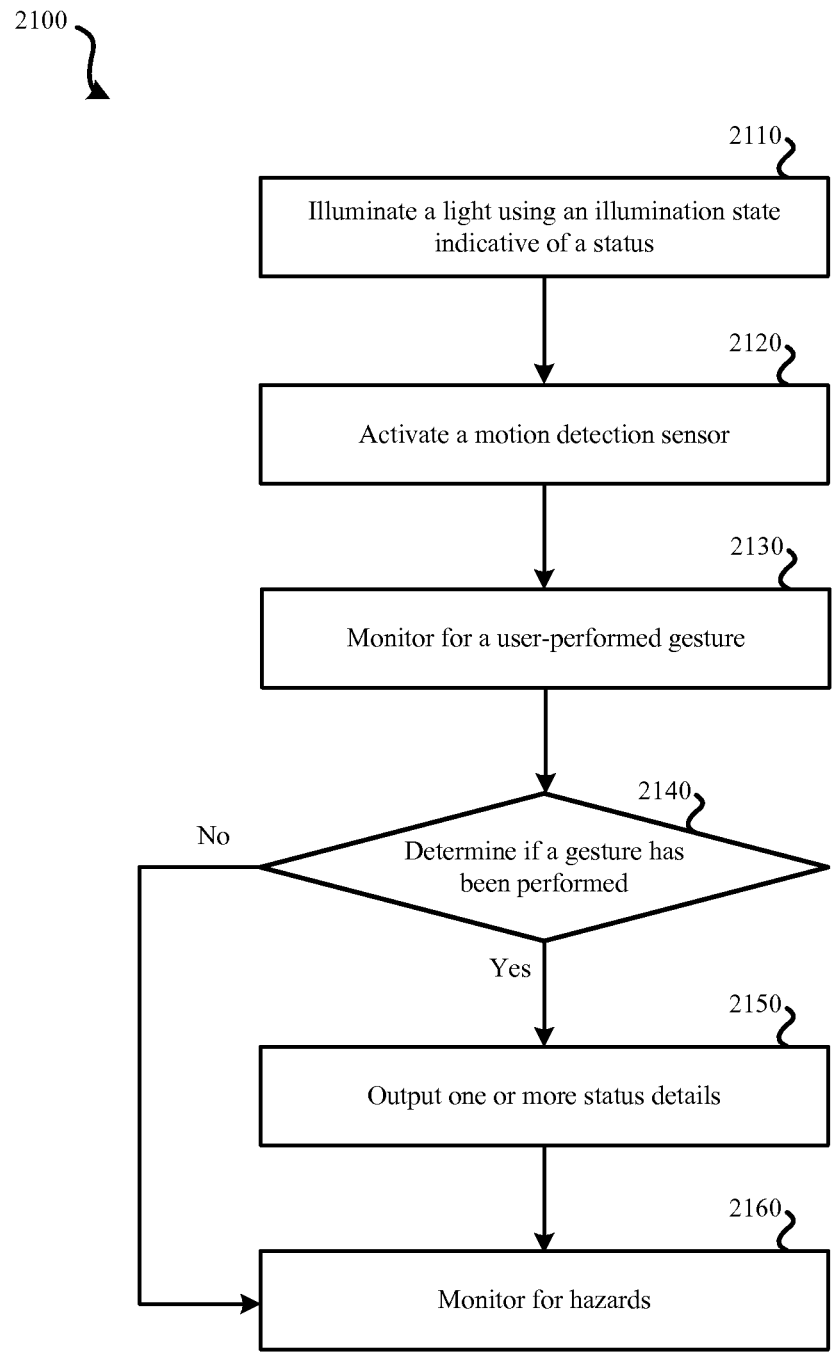
FIG. 21 illustrates an embodiment of a method for providing detail by a hazard detector about a status in response to a user-performed gesture.

FIG. 21 illustrates an embodiment of a method 2100 for providing detail about a status in response to user input. Method 2000 may be performed by a hazard detector following performing one of methods 1700 through 1900 or some other method for presenting a condition or status of the hazard detector. Each block of method 2000 may be performed by a hazard detector. Method 2000 may represent a more detailed embodiment of method 2000 of FIG. 20.

Block 2110 may represent the conclusion of methods 1700 through 1900. Block 2110 may require that a light of the hazard detector be illuminated according to an illumination state, the illumination state may be indicative of a status of the hazard detector. For instance, block 2110 may represent block 1750 of method 1700, block 1870 of method 1800, and/or block 1940 of method 1900. Block 2110 may also represent some other indication of a status being output. For instance, in some embodiments, block 2110 may be performed without at least one of methods 1700 through 1900 being performed.

At block 2120, one or more motion detector sensors may be activated for up to a predefined period of time. In some embodiments, the one or more motion detector sensors are continuously or at least already activated. Whether a motion detector needs to be activated at block 2120 may be dependent on whether the hazard detector is powered by a battery or via a structure power source. For instance, if powered by a battery, it may be desirable to conserve power such as to increase the longevity of the battery's life.

At block 2130, the hazard detector or other device may monitor for a gesture being performed by a user following the indication of the status being output at block 2110. In some embodiments, block 2130 may be triggered by some other condition occurring. For instance, the lighting condition reaching (e.g., decreasing to) a brightness level in the ambient environment of the hazard detector that matches or is below the threshold brightness level may serve as a trigger for block 2130. Monitoring for a gesture may include monitoring the output of the motion detection sensor for a specific gesture, such as a wave gesture, being performed once or more than once (for instance, multiple waves may be required). If the gesture is detected, the sensor may be disabled because no immediate future user input needs to be monitored for. Means for performing block 2130 may generally include a hazard detector (or other form of device). More specifically, means for performing block 2130 may include one or more processing devices, such as processors, and one or more sensors, such as a motion sensor.

At block 2140, it may be determined if the gesture which is being monitored at block 2130 has been performed. If not, method 2140 may proceed to block 2160. If the gesture has been determined to be performed, method 2100 may proceed to block 2150. Means for performing block 2130 may generally include a hazard detector (or other form of device). More specifically, means for performing block 2140 may include one or more processing devices, such as processors.

Blocks 2150 and 2160 may be performed similarly to blocks 2030 and 2040 of method 2000. As such, if the gesture is detected, the user is provided one or more details regarding the status of the hazard detector. If the gesture is not detected, the hazard detector continues monitoring for hazards without outputting one or more status details.

Figure 22:
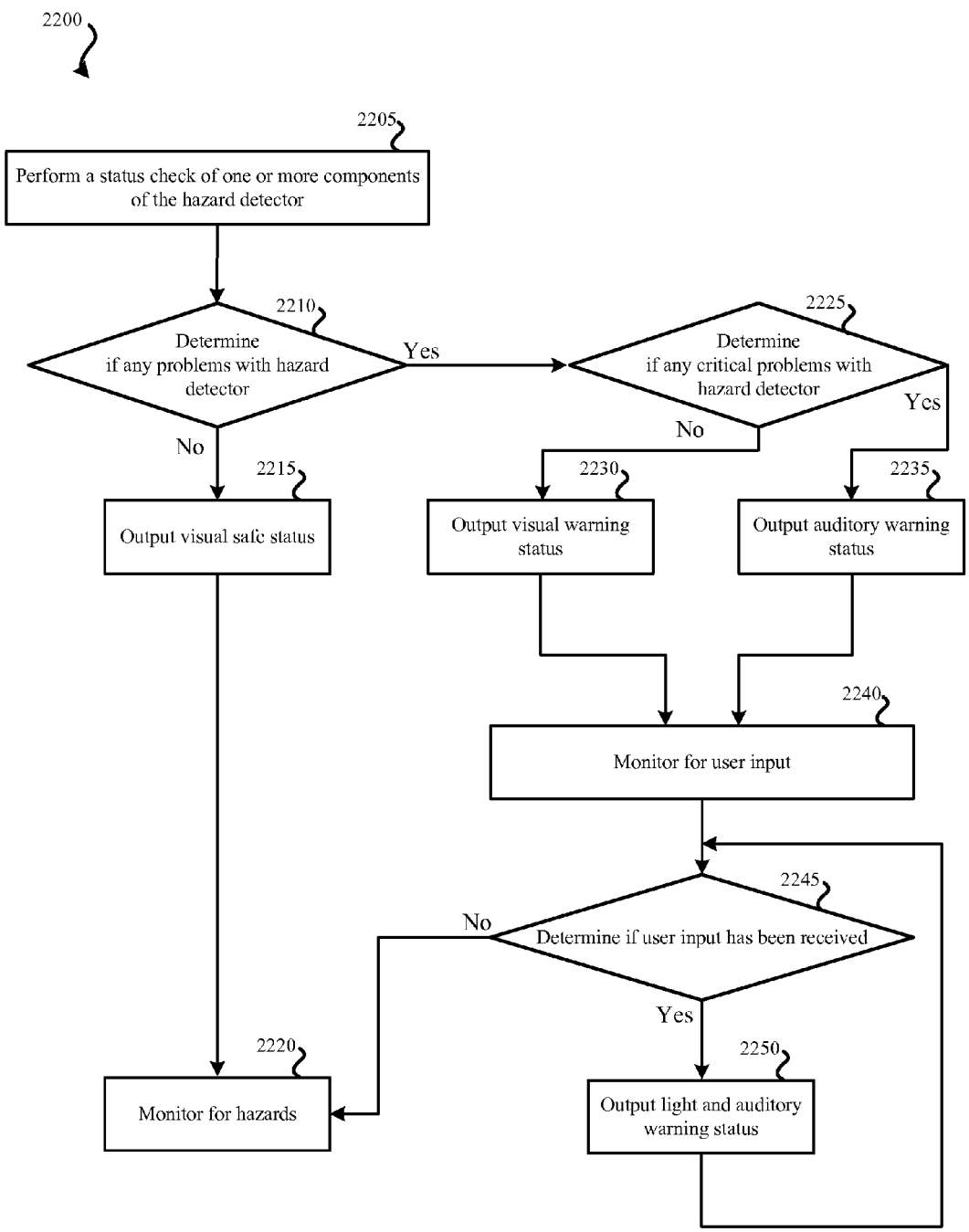
FIG. 22 illustrates an embodiment of a method for outputting a status based on user input and the criticality of the status.

FIG. 22 illustrates an embodiment of a method 2200 for outputting a status based on user input and the criticality of the status. Method 2200 may represent an alternate or more detailed embodiment of methods 1700, 1800, 2000, or 2100. Method 2200 represents various blocks which may be performed by a hazard detector, such as the hazard detector and/or other devices detailed in relation to FIGS. 1 through 6. It should be understood that blocks of method 2200 may be performed as part of other methods detailed in relation to FIGS. 17-20.

At block 2205, a status check of one or more components of the hazard detector may be performed. In some embodiments, the status check performed as part of block 2205 is performed in response to other blocks being performed, such as block 1720 (and, thus block 1710) of method 1700. Block 2205 may result in a similar analysis as is discussed in relation to block 1730. The status check of block 2205 may be divided up into an analysis of critical and non-critical status checks. Non-critical status checks may include determining if the battery is below a first threshold charge level, a message being present at a remote server in association with a user account linked with the hazard detector, the hazard detector is disconnected from the Internet (and was previously connected), the hazard detector is disconnected from a structure's power supply (and was previously connected), and/or some other problem occurred (an alphanumeric code may be assigned to such other problems). Critical status checks may include determining if the hazard detector has expired, determining if a hazard sensor has failed, and/or determining if the battery charge level is below a second threshold (which is representative of a lower charge level than the first threshold associated with the non-critical battery charge level).

If at block 2210, no status check results in a critical or non-critical status having a negative result, method 2200 may proceed to block 2215. At this block, a visual indication of there being no critical or non-critical status may be output, such as a green illumination of the light of the hazard detector using a calm animation, such as a pulse animation. Following block 2215, the hazard detector may not monitor for user input, such as a button press or gesture relevant to the status, and may proceed to block 2220 to continue to monitor for hazards.

If at block 2210, a status check results in a critical or non-critical status having a negative result (e.g., a sensor fails, the battery is low, Internet connectivity is lost, etc.), method 2200 may proceed to block 2225. At block 2225, if the status check resulted in a critical status, method 2200 may proceed to block 2235. At block 2235, an auditory warning status indicative of the critical status may be output. The auditory warning status may include a synthesized or recorded spoken message. The warning message may be accompanied by illumination of the hazard detector's light using a color indicative of a warning, such as yellow. An animation, such as a fast pulsing of the yellow light may be used to alert the user to the dangerous situation.

Returning to block 2225, if the status check resulted in a non-critical status, method 2200 may proceed to block 2230. At block 2230, a purely visual warning status indicative of the non-critical status may be output. The warning status may be illumination of the hazard detector's light using a color indicative of a warning, such as yellow. An animation, such as a slow pulsing of the yellow light may be used to alert the user to the quasi-dangerous situation. To learn the exact non-critical warning, the user may be required to provide user input.

At block 2240, user input, such as in the form of a button press of the hazard detector (or actuation of some other physical device on the hazard detector) or by a gesture being performed, may be monitored for by the hazard detector for up to a predefined period of time. For example, the hazard detector may monitor for input in response to the output status at blocks 2230 or 2235 for thirty seconds. If the user's presence is detected, the light of the hazard detector may be lit to indicate such presence, such as by illuminated or pulsing blue. At block 2245, it may be determined if input has been received. If no, method 2200 may proceed to block 2220. If yes, block 2250 may be performed.

At block 2250, the critical and/or non-critical statuses may be output via an auditory message. Such a message may include recorded or synthesized speech being output by the hazard detector. If the status was non-critical, block 2250 may be the first time the status is output via audio. If the status is critical, block 2250 may represent at least the second time the status is output via audio (due to block 2235). The auditory output may be accompanied by illumination of the hazard detector's light using a color indicative of a warning, such as yellow. An animation, such as a slow (for non-critical statuses) or fast (for critical statues) pulsing of the yellow light may be used to alert the user to the statues. Following block 2250, method 2200 may return to block 2245 to see if any additional user input is received, such as if the user wants the statuses to be repeated. Whether a gesture or a button push was performed by the user while block 2240 was being performed may alter how the hazard detector's light is lit at block 2250. For instance, if a button press was received at block 2240, the light may be lit blue and pulsed at a fast speed; if a gesture was detected at block 2240, the light may output a yellow wave animation (which may serve as an acknowledgement that the gesture was detected).

Figure 23:
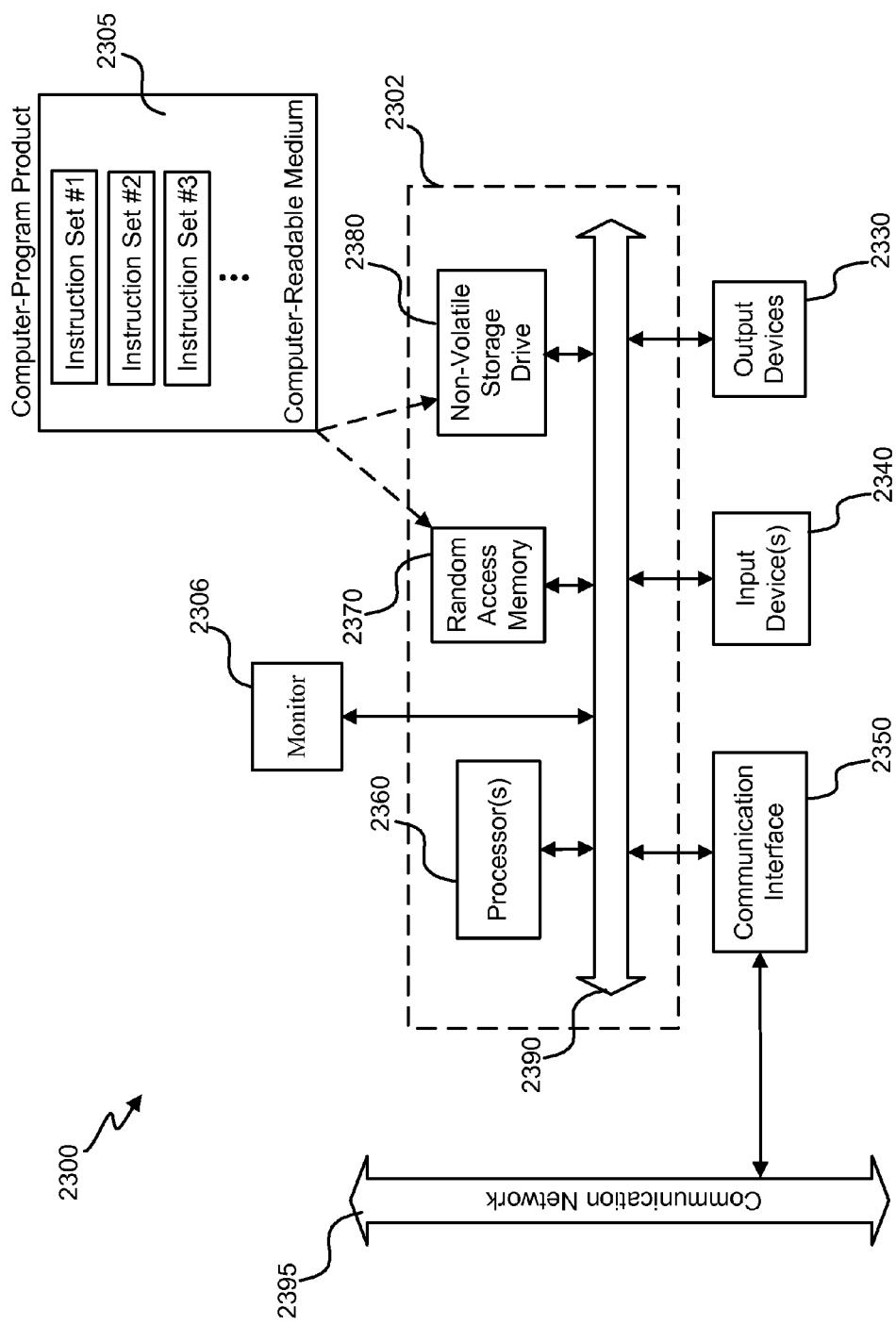
FIG. 23 illustrates an embodiment of a computer system.

With reference to FIG. 23, an embodiment of a special-purpose computer system 2300 is shown. For example, one or more intelligent components, processing engine 206 and components thereof may be a special-purpose computer system 2300. Such a special-purpose computer system 2300 may be incorporated as part of a hazard detector and/or any of the other computerized devices discussed herein, such as a remote server, smart thermostat, or network. The above methods may be implemented by computer-program products that direct a computer system to perform the actions of the above-described methods and components. Each such computer-program product may comprise sets of instructions (codes) embodied on a computer-readable medium that direct the processor of a computer system to perform corresponding actions. The instructions may be configured to run in sequential order, or in parallel (such as under different processing threads), or in a combination thereof. After loading the computer-program products on a general purpose computer system 2326, it is transformed into the special-purpose computer system 2300.

Special-purpose computer system 2300 comprises a computer 2302, a monitor 2306 coupled to computer 2302, one or more additional user output devices 2330 (optional) coupled to computer 2302, one or more user input devices 2340 (e.g., keyboard, mouse, track ball, touch screen) coupled to computer 2302, an optional communications interface 2350 coupled to computer 2302, a computer-program product 2305 stored in a tangible computer-readable memory in computer 2302. Computer-program product 2305 directs computer system 2300 to perform the above-described methods. Computer 2302 may include one or more processors 2360 that communicate with a number of peripheral devices via a bus subsystem 2390. These peripheral devices may include user output device(s) 2330, user input device(s) 2340, communications interface 2350, and a storage subsystem, such as random access memory (RAM) 2370 and non-volatile storage drive 2380 (e.g., disk drive, optical drive, solid state drive), which are forms of tangible computer-readable memory.

Computer-program product 2305 may be stored in non-volatile storage drive 2380 or another computer-readable medium accessible to computer 2302 and loaded into random access memory (RAM) 2370. Each processor 2360 may comprise a microprocessor, such as a microprocessor from Intel® or Advanced Micro Devices, Inc.®, or the like. To support computer-program product 2305, the computer 2302 runs an operating system that handles the communications of computer-program product 2305 with the above-noted components, as well as the communications between the above-noted components in support of the computer-program product 2305. Exemplary operating systems include Windows® or the like from Microsoft Corporation, Solaris® from Sun Microsystems, LINUX, UNIX, and the like.

User input devices 2340 include all possible types of devices and mechanisms to input information to computer 2302. These may include a keyboard, a keypad, a mouse, a scanner, a digital drawing pad, a touch screen incorporated into the display, audio input devices such as voice recognition systems, microphones, and other types of input devices. In various embodiments, user input devices 2340 are typically embodied as a computer mouse, a trackball, a track pad, a joystick, wireless remote, a drawing tablet, a voice command system. User input devices 2340 typically allow a user to select objects, icons, text and the like that appear on the monitor 2306 via a command such as a click of a button or the like. User output devices 2330 include all possible types of devices and mechanisms to output information from computer 2302. These may include a display (e.g., monitor 2306), printers, non-visual displays such as audio output devices, etc.

Communications interface 2350 provides an interface to other communication networks, such as communication network 2395, and devices and may serve as an interface to receive data from and transmit data to other systems, WANs and/or the Internet. Embodiments of communications interface 2350 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 2350 may be coupled to a computer network, to a FireWire® bus, or the like. In other embodiments, communications interface 2350 may be physically integrated on the motherboard of computer 2302, and/or may be a software program, or the like.

RAM 2370 and non-volatile storage drive 2380 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 2370 and non-volatile storage drive 2380 may be configured to store the basic programming and data constructs that provide the functionality of various embodiments of the present invention, as described above.

Software instruction sets that provide the functionality of the present invention may be stored in RAM 2370 and non-volatile storage drive 2380. These instruction sets or code may be executed by the processor(s) 2360. RAM 2370 and non-volatile storage drive 2380 may also provide a repository to store data and data structures used in accordance with the present invention. RAM 2370 and non-volatile storage drive 2380 may include a number of memories including a main random access memory (RAM) to store instructions and data during program execution and a read-only memory (ROM) in which fixed instructions are stored. RAM 2370 and non-volatile storage drive 2380 may include a file storage subsystem providing persistent (non-volatile) storage of program and/or data files. RAM 2370 and non-volatile storage drive 2380 may also include removable storage systems, such as removable flash memory.

Bus subsystem 2390 provides a mechanism to allow the various components and subsystems of computer 2302 to communicate with each other as intended. Although bus subsystem 2390 is shown schematically as a single bus, alternative embodiments of the bus subsystem may utilize multiple busses or communication paths within the computer 2302.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known, processes, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

It is to be appreciated that while the described methods and systems for intuitive status signaling at opportune times for a hazard detector are particularly advantageous in view of the particular device context, in that hazard detectors represent important life safety devices, in that hazard detectors are likely to be placed in many rooms around the house, in that hazard detectors are likely to be well-positioned for viewing from many places in these rooms, including from near light switches, and in that hazard detectors will usually not have full on-device graphical user interfaces but can be outfitted quite readily with non-graphical but simple, visually appealing on-device user interface elements (e.g., a simple pressable button with shaped on-device lighting), and in further view of power limitations for the case of battery-only hazard detectors making it desirable for status communications using minimal amounts of electrical power, the scope of the present disclosure is not so limited. Rather, the described methods and systems for intuitive status signaling at opportune times are widely applicable to any of a variety of smart-home devices such as those described in relation to FIG. 15 supra and including, but not limited to, thermostats, environmental sensors, motion sensors, occupancy sensors, baby monitors, remote controllers, key fob remote controllers, smart-home hubs, security keypads, biometric access controllers, other security devices, cameras, microphones, speakers, time-of-flight based LED position/motion sensing arrays, doorbells, intercom devices, smart light switches, smart door locks, door sensors, window sensors, generic programmable wireless control buttons, lighting equipment including night lights and mood lighting, smart appliances, entertainment devices, home service robots, garage door openers, door openers, window shade controllers, other mechanical actuation devices, solar power arrays, outdoor pathway lighting, irrigation equipment, lawn care equipment, or other smart home devices. Although widely applicable for any of such smart-home devices, one or more of the described methods and systems become increasingly advantageous when applied in the context of devices that may have more limited on-device user interface capability (e.g., without graphical user interfaces), and/or having power limitations that make it desirable for status communications using minimal amounts of electrical power, while being located in relatively readily-viewable locations and/or well-traveled locations in the home. Having read this disclosure, one having skill in the art could apply the methods and systems of the present invention in the context of one or more of the above-described smart home devices. Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

It is to be further appreciated that the described methods and systems for intuitive status signaling at opportune times for a hazard detector are particularly advantageous for hazard detectors that are network-connected, in that the status communications can relate to both intrinsic hazard detector status as well as any non-hazard-detector related status information that the hazard detector might be able to receive from other home devices, from the cloud service, or from any other network-connected or internet-connected data source. Thus, by way of example, in addition to the examples given supra in the instant application, the hazard detector could provide an alertive-color status if a certain notable security condition in the home (e.g., there is a downstairs window open, the back garage door is not locked, etc.), or there is a certain notable maintenance condition in the home (e.g., the HVAC filter needs replacing, a front porch lamp bulb needs replacing, etc.), or there is some other notable status, condition, pattern of activity, or concurrent activity in the home (e.g., the living room television is on but there has not been any person in the living room for 20 minutes, the family dog has been standing at the back door for 15 minutes, etc.). However, it is within the scope of the present teachings to provide a stand-alone, non-network-connected hazard detector that simply communicates its own status to the user at the opportune times, and that optionally looks for follow-up signals from the user by gesture, voice, etc., and provides further information about its own status upon request. Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A hazard detector, comprising:
   at least one hazard detection sensor that detects a presence of at least one type of hazard;
   a light sensor that senses a brightness level in an ambient environment of the hazard detector;
   a light; and
   a processing system provided in operative communication with the at least one hazard detection sensor, the light sensor, and the light, the processing system configured to:
      receive an indication of the brightness level in the ambient environment of the hazard detector from the light sensor;
      determine whether the indication of the brightness level is indicative of a dimming of one or more illumination sources in the ambient environment;
      access, responsive to an indication of the dimming of the one or more illumination sources, information representative of a status of one or more components of the hazard detector;
      select an illumination state from a plurality of illumination states based on the accessed information representative of the status of the one or more components of the hazard detector; and
      cause the light to illuminate using the selected illumination state of the plurality of illumination states.

2. The hazard detector of claim 1, wherein the at least one hazard detection sensor comprises a smoke detection sensor and a carbon monoxide detection sensor.

3. The hazard detector of claim 1, wherein the processing system is further configured to:
   determine whether a battery charge of a battery of the hazard detector is below a threshold charge level, wherein the selected illumination state is indicative of a low battery condition.

4. The hazard detector of claim 1, wherein each illumination state of the plurality of illumination states comprises at least a color and an animation pattern.

5. The hazard detector of claim 1, wherein the processing system is configured to cause the illumination state to comprise:
   gradually increasing a brightness level of the light for at least 0.5 seconds;
   maintaining the brightness level of the light for at least 0.5 seconds; and
   gradually decreasing the brightness level of the light for at least 0.5 seconds.

6. The hazard detector of claim 1, further comprising:
   a wireless transceiver configured to communicate with a wireless network, wherein the processing system is further configured to transmit a request to a remote server system accessible via the wireless transceiver and the Internet.

7. The hazard detector of claim 6, wherein the processing system is further configured to:
   receive a notification from the remote server system via the wireless transceiver, wherein the illumination state is selected by the processing system based on the status check of the one or more components of the hazard detector and the notification from the remote server system received via the wireless transceiver.

8. The hazard detector of claim 1, wherein the light comprises at least five light emitting diodes (LEDs) that output light from the hazard detector in a circular pattern.

9. The hazard detector of claim 8, further comprising:
   a button configured to be actuated by a user to initiate a function of the hazard detector, wherein the plurality of LEDs are arranged to output light from the hazard detector in the circular pattern encircling the button.

10. The hazard detector of claim 1, wherein the processing system is further configured to:
    determine, responsive to an indication of the dimming of the one or more illumination sources, that at least a threshold time period has elapsed since previously causing the light to illuminate, wherein the processing system being configured to cause the light to illuminate based on the illumination state further comprises the processing system being configured to cause the light to illuminate based on at least the threshold time period having been determined to have elapsed.

11. The hazard detector of claim 1, further comprising:
    a motion detection sensor that senses motion in the ambient environment of the hazard detector, wherein the processing system is further configured to:
       cause the light to illuminate based on the motion detector indicating motion is present in the ambient environment of the hazard detector and responsive to the indication of the dimming of the one or more illumination sources.

12. The hazard detector of claim 11, wherein the processing system is configured to:
    cause the light to illuminate based on the motion detector indicating motion is present in the ambient environment of the hazard detector, responsive to the indication of the dimming of the one or more illumination sources, and a user-defined setting stored by the processing system indicative of the hazard detector being not inside a bedroom.

13. A method for outputting a status of a hazard detector, the method comprising:
    measuring, by the hazard detector, a brightness level in the ambient environment of the hazard detector;

determining, by the hazard detector, whether the brightness level in the ambient environment of the hazard detector is indicative of a dimming of an illumination source;
accessing, responsive to determining the brightness level in the ambient environment is indicative of the dimming of the illumination source, information representative of a status of the hazard detector;
selecting, by the hazard detector, an illumination state from a plurality of illumination states based on the information representative of the status of the hazard detector; and
causing, by the hazard detector, a light of the hazard detector to illuminate using the selected illumination state of the plurality of illumination states.

14. The method for outputting the status of the hazard detector of claim 13, wherein the hazard detector comprises a smoke detection sensor and a carbon monoxide detection sensor and the method further comprises:
performing, by the hazard detector, a status check of one or more components of the hazard detector, which comprises checking a status of the smoke detection sensor and the carbon monoxide detection sensor, wherein the information representative of the status of the hazard detector is representative of the status of the smoke detection sensor and the carbon monoxide detection sensor.

15. The method for outputting the status of the hazard detector of claim 13, further comprising:
wirelessly communicating, by the hazard detector, with a wireless network, to transmit a request to a remote server system accessible via the wireless network and the Internet.

16. The method for outputting the status of the hazard detector of claim 15, further comprising:
receiving, by the hazard detector, via the wireless network, a notification from the remote server system, wherein the illumination state is selected by the processing system based on notification from the remote server system received via the wireless network.

17. The method for outputting the status of the hazard detector of claim 13, the method further comprising:
determining, by the hazard detector, that at least a threshold time period has elapsed since previously causing the light to illuminate in response to determining that the brightness level is indicative of the dimming of the illumination source; wherein causing, by the hazard detector, the light to illuminate based on the illumination state is further based on at least the threshold time period having been determined to have elapsed.

18. The method for outputting the status of the hazard detector of claim 13, wherein causing the light of the hazard detector to illuminate using the selected illumination state of the plurality of illumination states further comprises:
gradually increasing a brightness level of the light for at least 0.5 seconds;
maintaining the brightness level of the light for at least 0.5 seconds; and
gradually decreasing the brightness level of the light for at least 0.5 seconds.

19. A hazard detector apparatus, comprising:
means for measuring a brightness level in the ambient environment of the hazard detector apparatus;
means for determining whether the brightness level in the ambient environment of the hazard detector apparatus is indicative of a dimming of an illumination source;
means for accessing, responsive to determining the brightness level in the ambient environment is indicative of the dimming of the illumination source, information representative of a status of the hazard detector apparatus;
means for selecting an illumination state from a plurality of illumination states based on the information representative of the status of the hazard detector apparatus; and
means for causing a lighting means of the hazard detector to illuminate using the selected illumination state of the plurality of illumination states.

20. The hazard detector apparatus of claim 19, further comprising:
means for wirelessly communicating with a wireless network, to transmit a request to a remote server system accessible via the wireless network and the Internet; and
means for receiving, via the wireless network, a notification from the remote server system, wherein:
the illumination state is selected based on the notification from the remote server system received via the wireless network.

* * * * *